United States Patent
Hendriks et al.

(10) Patent No.: US 12,089,821 B2
(45) Date of Patent: Sep. 17, 2024

(54) ORTHOPEDIC PIN FOR OPTICALLY ANALYZING A BONE REGION

(71) Applicant: KONINKLIJKE PHILIPS N.V., Eindhoven (NL)

(72) Inventors: Bernardus Hendrikus Wilhelmus Hendriks, Eindhoven (NL); Drazenko Babic, Best (NL); Jarich Willem Spliethoff, Utrecht (NL); Gerhardus Wilhelmus Lucassen, Eindhoven (NL); Joanneke Gerrigje Groen, Veldhoven (NL); Christian Reich, Eindhoven (NL); Ronaldus Frederik Johannes Holthuizen, Culemborg (NL); Robert Johannes Frederik Homan, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 156 days.

(21) Appl. No.: 17/637,830

(22) PCT Filed: Aug. 28, 2020

(86) PCT No.: PCT/EP2020/074082
§ 371 (c)(1),
(2) Date: Feb. 24, 2022

(87) PCT Pub. No.: WO2021/038042
PCT Pub. Date: Mar. 4, 2021

(65) Prior Publication Data
US 2022/0280033 A1    Sep. 8, 2022

(30) Foreign Application Priority Data

Aug. 29, 2019 (EP) .................................... 19194437
Apr. 24, 2020 (EP) .................................... 20171382

(51) Int. Cl.
*A61B 1/317* (2006.01)
*A61B 1/00* (2006.01)
(Continued)

(52) U.S. Cl.
CPC .......... *A61B 1/317* (2013.01); *A61B 1/00126* (2013.01); *A61B 1/00165* (2013.01);
(Continued)

(58) Field of Classification Search
CPC . A61B 1/317; A61B 1/00126; A61B 1/00165; A61B 5/0075; A61B 5/4504;
(Continued)

(56) References Cited

U.S. PATENT DOCUMENTS

2002/0104196 A1* 8/2002 Geiger ............... B65D 63/1072
24/16 PB
2018/0153623 A1* 6/2018 Noonan ............... A61B 17/848

FOREIGN PATENT DOCUMENTS

CN   101791246 A   8/2010
WO   2017055144 A1  4/2017

OTHER PUBLICATIONS

International Search Report and Written Opinion of PCT/EP2020/074082, dated Jan. 15, 2021.
(Continued)

*Primary Examiner* — Michael P Mooney

(57) ABSTRACT

An orthopedic pin (100) for optically analyzing a bone region (110) includes an elongate shaft (101) and at least one optical fiber (105). The elongate shaft has a circular outer cross section with a first diameter (D1), a distal end (102) for insertion into bone, a proximal end (103), and an optical connector portion (104) disposed towards the proximal end (103). The at least one optical fiber (105) extends within the elongate shaft (101) between the optical connector portion (104), and the distal end (102) for transmitting optical
(Continued)

radiation between the optical connector portion (104) and the bone region (110) when the distal end (102) is inserted into the bone region (110). The optical connector portion (104) comprises a reduced-diameter portion (106). The reduced-diameter portion (106) extends along at least a portion of the elongate shaft (101), and has an outer cross section comprising a width (Drd) perpendicularly with respect to the elongate shaft (101). The width (Drd) is less than the first diameter (D1).

15 Claims, 12 Drawing Sheets

(51) Int. Cl.
    *A61B 5/00*     (2006.01)
    *A61B 17/84*     (2006.01)
    *A61B 17/88*     (2006.01)
    *A61B 17/92*     (2006.01)

(52) U.S. Cl.
    CPC .......... *A61B 5/0075* (2013.01); *A61B 5/4504* (2013.01); *A61B 5/6878* (2013.01); *A61B 17/848* (2013.01); *A61B 17/8897* (2013.01); *A61B 2017/922* (2013.01)

(58) Field of Classification Search
    CPC ... A61B 5/6878; A61B 17/848; A61B 17/922; A61B 17/8897
    See application file for complete search history.

(56) References Cited

OTHER PUBLICATIONS

Mobbs, Ralph J. et al "Techique,. Challenges and Indications for Percutaneous Pedicle Screw Fixation", Journal of Clinical Neuroscience, vol. 18, 2011, pp. 741-749.

Nachabe, Rami et al "Estimation of Biological Chromophores using Diffuse Optical Spectroscopy: Benefit of Extending the UV-VIS wavelength range to include 1000 to 1600 nm", Optical Express, vol. 18, No. 24, 2010.

Nachabe, Rami et al "Estimation of Lipid and Water Concentrations in Scattering Media with Diffuse Optical Spectroscopy from 900 to 1600 nm", Journal of Biomedical Optics, vol. 15, No. 3, 2010, pp. 037015-10.

Muller, M. et al "Recovering Intrinsic Fluorescence by Monte Carlo Modeling", Journal Biomedical Optics, vol. 18, 2013, pp. 027009-1-027009-13.

Farrel, T.J. et al "A Diffusion Theory Model of Spatially Resolved, Steady-State Diffuse Reflectance for the Non-Invasive Determination of Tissue Optical Properties", Medical Physics, vol. 19, 1992, pp. 879-888.

* cited by examiner

ORTHOPEDIC PIN FOR OPTICALLY ANALYZING A BONE REGION

CROSS-REFERENCE TO PRIOR APPLICATIONS

This application is the U.S. National Phase application under 35 U.S.C. § 371 of International Application No. PCT/EP2020/074082, filed on Aug. 28, 2020, which claims the benefit of European Patent Application No. 19194437.0, filed on Aug. 29, 2019 and European Patent Application No. 20171382.3, filed Apr. 24, 2020. These applications are hereby incorporated by reference herein.

FIELD OF THE INVENTION

The invention relates to an orthopedic pin for optically analyzing a bone region. A related optical adapter, a handheld surgical tool and a kit are also disclosed. The invention finds application in the general field of orthopedic surgery, and more particularly in the field of spine surgery. In the latter, the orthopedic pin may for example be used to guide the placement of a pedicle screw.

BACKGROUND OF THE INVENTION

In many medical procedures an implantable device is inserted into bone tissue. For example, bone fixation devices are often used to position bone tissue in relation to other bone tissue or in relation to an external surrounding.

Examples of such medical procedures include pedicle screw insertions in the cervical, thoracic and lumbar spine, fracture fixations in various bone traumas, and plate positioning in hip and knee arthroplasties.

Pedicle screw fixations, as described in a document by Mobbs, R. J., Sivabalan, P., and Li, J., entitled *"Technique, challenges and indications for percutaneous pedicle screw fixation"*, Journal of Clinical Neuroscience 18 (2011) pp. 741-749 are a mainstay in the treatment of spinal degenerative disease, intervertebral disc disease, spinal traumas and spinal deformities. Pedicle screw fixation provides short, rigid segmental stabilization that preserves motion segments and stabilizes the spine. Fusion rates and clinical outcome in the treatment of thoracolumbar fractures appear to be superior to that achieved using other forms of treatment. According to a report by the Agency for Healthcare Research and Quality (AHRQ), approximately 488,000 spinal fusions were performed during U.S. hospital stays in 2011 (a rate of 15.7 stays per 10,000 population), which accounted for 3.1% of all operating room procedures.

Despite its worldwide use in enhancing spine stabilization, the safety and effectiveness of pedicle-screw instrumentation has been questioned. A major concerns relates to the accuracy of pedicle screw placement. Pedicle screws are often inserted either blindly or under often-poor fluoroscopic guidance, thus leaving significant room for improvement.

In this respect, document WO 2017/055144 A1 describes a system for implanting an implantable device in bone tissue, a processing unit for such system, a method of implanting an implantable device and a method of providing information for an implanting of an implantable device. In view of the finding that a fat content in cancellous bone is higher than a fat content in compact bone, the lipids fraction, which can be determined by optical means, e.g. spectroscopy, can be used to determine correct screw placement in healthy bone. In one embodiment, document WO 2017/055144 A1 describes a pedicle screw with a hollow shaft, and into which an optical stylet may be inserted. The optical stylet extends to the distal tip of the screw and includes an optical fiber that is used to make optical measurements at the distal tip of the screw. The fat content of the (bone) tissue in front of the tip of the screw is determined via spectroscopic analysis and used to determine whether the (bone) tissue is that of the soft(er) part of the bone or the hard(er) part of the bone to assist in placing the screw. Document WO 2017/055144 A1 also discloses that the optical sensing part may be integrated in a Kirschner wire, i.e. a K-wire, in procedures that involve the initial placement of a K-wire in the bone.

Despite these advances there remains room to provide improved guidance to a physician when placing a bone implantation device such as a pedicle screw.

US 2018/0153623 discloses an insert for a plurality of different surgical instruments with each surgical instrument including a lumen. The insert has aa Fiber-Optic Realshape (trade mark) sensor for generating sensing data indicative of a reconstructed shape of a tracking segment of the sensor. The plurality of surgical instruments may be a same version or different versions of a same instrument type of surgical instrument (e.g., same sized k-wires and/or different sized k-wires), or different instrument types of surgical instruments (e.g., a j-needle and an awl).

SUMMARY OF THE INVENTION

The invention seeks to provide an improved device for guiding the placement of a bone implantation device such as a pedicle screw. Thereto an orthopedic pin for optically analyzing a bone region is provided. An optical adapter, a handheld surgical tool and a kit are also provided. The orthopedic pin includes an elongate shaft and at least one optical fiber. The elongate shaft has a circular outer cross section with a first diameter, a distal end for insertion into bone, a proximal end, and an optical connector portion disposed towards the proximal end. The at least one optical fiber extends within the elongate shaft between the optical connector portion, and the distal end for transmitting optical radiation between the optical connector portion and the bone region when the distal end is inserted into the bone region. The optical connector portion includes a reduced-diameter portion. The reduced-diameter portion extends along at least a portion of the elongate shaft, and has an outer cross section comprising a width perpendicularly with respect to the elongate shaft. The width is less than the first diameter.

Since the width in the reduced-diameter portion is less than the first diameter it may be used for gripping the elongate shaft. It may for example be used for releasably mating the orthopedic pin with a counterpart optical connector such as an optical adapter. The orthopedic pin benefits from improved manufacturability since material removal methods such as grinding may be used to form the reduced-diameter portion of the optical connector portion. Since in the reduced-diameter portion the width is less than the first diameter, a means for gripping the elongate shaft is provided without widening the elongate shaft. The outer cross section of the proximal end of the elongate shaft is thus within the outer cross section of the elongate shaft where its cross section is determined by the first diameter. This allows the proximal end of the orthopedic pin to be slideably received within a channel of a surgical device such as a bone drill bit, a surgical hammer, or a bone fixation device such as a pedicle screw, without the need to modify the surgical device. This may also improve workflow during a medical procedure. For example, in a first stage of a pedicle screw insertion procedure a pilot hole may be provided in a bone region by hammering the orthopedic pin into the bone region using a surgical hammer. In a second stage of the pedicle screw insertion procedure a pedicle screw may be slid over the distal end of the orthopedic pin, which serves as a guide. In the first stage the orthopedic pin is received in a channel of the surgical hammer, and during its insertion the bone region is optically analyzed by an optical system coupled to the orthopedic pin. After a suitable pilot hole has been provided by the orthopedic pin, the reduced-diameter portion permits the optical system to be de-coupled from the orthopedic pin by sliding the channel of the surgical hammer over the proximal end of the orthopedic pin in order to subsequently carry out the second stage of the procedure without removing the orthopedic pin from the bone region. Workflow is improved by providing an optical connector portion that obviates the need to remove the orthopedic pin from the bone region between the first hammering stage, and the second pedicle screw insertion stage. Further advantages will also be apparent to the skilled person.

Further aspects and their advantages are described with reference to the dependent claims. Further advantages from these aspects will also be apparent to the skilled person.

DETAILED DESCRIPTION OF THE INVENTION

Figure 1A:
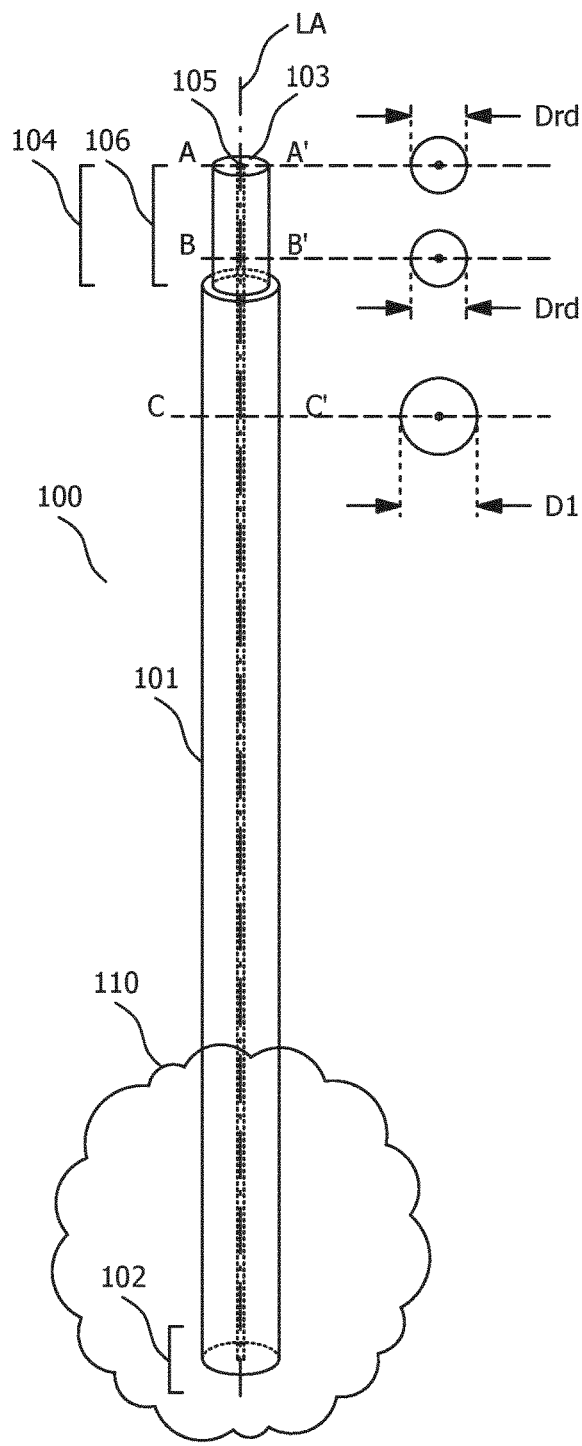
FIG. 1A illustrates an orthopedic pin 100 for optically analyzing a bone region 110.

In order to illustrate the principles of the present invention an orthopedic pin is described with particular reference to a medical procedure involving the insertion of a bone fixation device in the form of a pedicle screw. Reference is made to an orthopedic pin in the specific form of a K-wire, this type of orthopedic pin being used routinely in spinal surgery field to provide, by hammering, and subsequently guide, by being slideably received within the channel of a hollow pedicle screw, the insertion of the pedicle screw. It is however to be appreciated that the invention also finds application in other medical procedures than the insertion of a bone fixation device, including for example the insertion of a bone implantable device in general. The term orthopedic pin refers in general to an elongate device used fix bone elements or to guide a surgical tool for use in spinal or orthopedic surgery. Thus, the invention also finds application in other types of orthopedic pins than a K-wire, including but not limited to a Steinmann pin and a trocar. Moreover, it is to be appreciated that the orthopedic pin finds application in guiding the insertion of surgical devices in general into bone, including but not limited to surgical devices such as a surgical drill bit, a surgical hammer, a screwdriver, a dilator and an awl, as well as other bone fixation devices than a pedicle screw, such as bone screws in general. Thus, it is contemplated that the orthopedic pin may be used to guide the insertion of medical devices in general into bone regions in general, and its application is not limited to surgical interventions involving the spine.

As described in the document by Mobbs, R. J., Sivabalan, P., and Li, J., entitled *"Technique, challenges and indications for percutaneous pedicle screw fixation"*, Journal of Clinical Neuroscience 18 (2011) pp. 741-749, one process for the percutaneous insertion of a pedicle screw involves the following steps:
  (i) Place an intra-operative radiography image intensifier in the anterior/posterior position. The spinous process should be midline between the pedicles to ensure a direct anterior/posterior projection.
  (ii) Mark the position of the lateral aspect of the pedicle on the skin. Depending upon the depth of the tissue between skin and pedicle, the skin incision should be made laterally so that a Jamshidi needle can be angled appropriately when inserting it into the pedicle.
  (iii) Place the Jamshidi needle through the skin incision and "dock" onto the lateral aspect of the pedicle.
  (iv) Advance the Jamshidi needle 20 mm to 25 mm into the pedicle, making sure the needle remains lateral to the medial pedicle wall.
  (v) Position the intra-operative radiography image intensifier in the lateral plane. The Jamshidi needle should now be in the vertebral body, and therefore "safe" with no risk of medial pedicle breach.
  (vi) Place a K-wire down the Jamshidi needle and place a pedicle tap down the trajectory of the K-wire.
  (vii) Place the final pedicle screw with the screw placed down the K-wire, making sure not to advance the K-wire beyond the anterior aspect of the vertebral body.

In the above-described method the goal of the surgeon is to ultimately locate the pedicle screw in the relatively softer core tissue of the vertebra termed "cancellous bone" as compared to in the relatively harder shell portion of the vertebra, termed "cortical bone". Serious medical complications may arise if the surgeon inadvertently punctures the cortical bone, i.e. "breaches" the pedicle, particularly just after initially entering the pedicle and whilst navigating along the neck of the pedicle, as well as at the anterior aspect of the vertebral body. The above-described method of placing a pedicle screw relies heavily on the use of intra-operative radiography images in order to avoid these hazards, and suffers from the continual need to adjust the orientation of the X-ray imaging system. It also suffers from the additional hazard of X-ray dose to the patient and physician.

In the present invention, an orthopedic pin is provided that may be used to improve the guidance of the placement of a pedicle screw using the above-described and other related medical procedures. As mentioned above, the inventive orthopedic pin may be provided in the form of a K-wire, which may take the place of the K-wire described in the above steps in order to guide the subsequent placement of the pedicle screw. As described in more detail below; the inventive K-wire may in general be used in combination with various surgical tools to provide a properly-oriented pilot hole that ultimately allows for the subsequent insertion of a pedicle screw or other bone implant.

Thereto, FIG. 1A illustrates an orthopedic pin 100 for optically analyzing a bone region 110. Orthopedic pin 100 includes optical fiber 105 and elongate shaft 101. Elongate shaft 101 has a circular outer cross section with a first diameter D1, a distal end 102 for insertion into bone, a proximal end 103, and an optical connector portion 104 disposed towards proximal end 103. Longitudinal axis LA of elongate shaft 101 is also illustrated in FIG. 1A; wherein circular outer cross section with first diameter D1 lies is in a plane that is perpendicular with respect to longitudinal axis LA. In order to facilitate the insertion of distal end 102 into bone, distal end 102 may for example include at least one beveled surface, or a rounded profile, and may thus deviate from the illustrated perpendicular endface, which is also suitable for this purpose. Optical fiber 105 extends within elongate shaft 101 between optical connector portion 104 and distal end 102 and is adapted for transmitting optical radiation between the optical connector portion 104 and bone region 110 when distal end 102 is inserted into the bone region 110.

At proximal end 103, a proximal endface of optical fiber 105 is exposed for coupling optical radiation between an optical source and/or detector (not illustrated) and optical fiber 105. At distal end 103, a distal endface of optical fiber 105 is exposed for coupling optical radiation between optical fiber 105 and bone region 110. In so doing, when optical fiber 105 is coupled to the optical source (not illustrated) by means of optical connector portion 104, and when distal end 102 is inserted into bone region 110, optical radiation generated by the optical source may irradiate bone region 110 via optical fiber 105, and optical radiation reflected or scattered by bone region 110 may be coupled back along optical fiber to an optical detector (not illustrated) that is coupled to optical connector portion 104, and whereupon a spectral analysis of the detected optical radiation may be carried out as described hereinbelow in order to determine a type of bone region 110, or more specifically to discriminate between the bone region being one of cortical and cancellous bone.

With further reference to FIG. 1A, optical connector portion 104 includes reduced-diameter portion 106. Reduced-diameter portion 106 extends along at least a portion of elongate shaft 101, and has an outer cross section comprising a width Drd perpendicularly with respect to elongate shaft 101. Width Drd is less than first diameter D1 in order to grip elongate shaft 101, for example for releasably mating the orthopedic pin with a counterpart optical connector such as an optical adapter.

Advantageously, reduced diameter portion 106 permits the gripping of elongate shaft 101 such that optical connector portion 104 may be releasably mated with a counterpart optical connector such as an optical adapter (not shown). Since width Drd is less than first diameter D1, elongate shaft 101 may be gripped without the need to widen elongate shaft 101. This improves the manufacturability of optical connector portion 104; in particular because material removal methods may be used to provide width Drd. Moreover, since the proximal end of elongate shaft 101 is not widened to provide optical connector portion 104, i.e. it is no wider than first diameter D1, elongate shaft 101 may be slideably received, specifically over proximal end 103, within a channel of a surgical tool such as a bone drill bit or hammer or a bone fixation device such as a pedicle screw, during the provision of a pilot hole in bone region 110 or during the subsequent insertion of a bone fixation device into bone region 110, without the need to modify the surgical tool or pedicle screw.

Thus, orthopedic pin 100 facilitates optical sensing of the type of (bone) tissue at distal end 102 of orthopedic pin 100, thereby assisting the physician in the various steps of placing a bone implant such as a pedicle screw into bone region 110. As compared to the use of a conventional K-wire under X-ray imaging, the optical guidance as facilitated by orthopedic pin 100 may be considered to offer improved sensitivity to the proximity of cortical bone, thereby offering improved accuracy in positioning distal end 102 in relation to cortical bone, and with reduced, or even no, X-ray radiation dose.

Figure 1B:
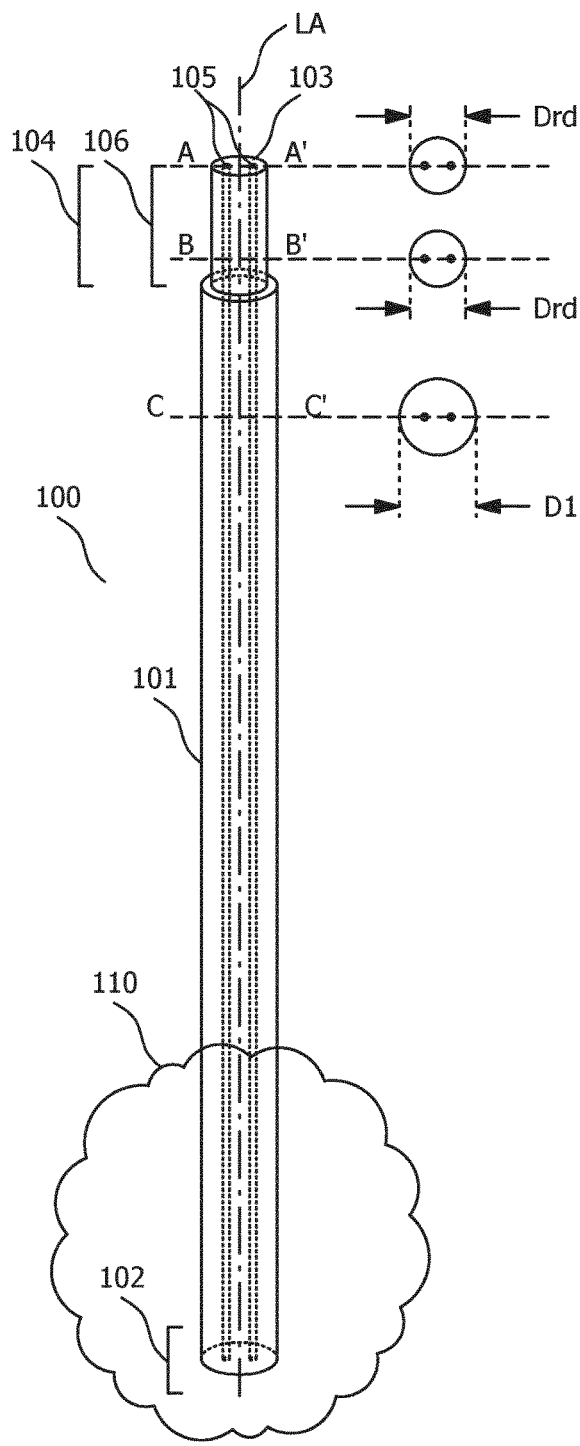
FIG. 1B illustrates an orthopedic pin 100 having two optical fibers 105 for optically analyzing a bone region 110.

FIG. 1B illustrates an orthopedic pin 100 having two optical fibers 105 for optically analyzing a bone region 110. FIG. 1B is identical to FIG. 1A except for having two optical fibers. The proximal endfaces of optical fibers 105 are exposed for receiving optical radiation from an optical source (not illustrated) and the distal endfaces of optical fibers 105 are exposed for coupling the optical radiation to and/or from bone region 110. In operation, one of optical fibers 105 may be coupled to the optical source by means of optical connector portion 104, and when distal end 102 is inserted into bone region 110, optical radiation generated by the optical source may irradiate bone region 110 via one of optical fibers 105, and optical radiation reflected or scattered by bone region 110 may be coupled into the other of optical fibers 105 and back along said optical fiber to an optical detector (not illustrated) that is coupled to optical connector portion 104, and whereupon a spectral analysis of the detected optical radiation may be carried out as described hereinbelow in order to determine a type of bone region 110, or more specifically to discriminate between the type being one of cortical and cancellous bone.

As compared to FIG. 1A, the use of two optical fibers illustrated in FIG. 1B permits the delivery of optical radiation to bone region 110 to be separated from the detection of optical radiation from bone region 110. This prevent the contamination of detected optical radiation that is collected from bone region 110 by back-reflections of optical source radiation at the distal end of the optical fiber when a single optical fiber is used to both deliver and detect optical radiation. Moreover, the use of separate delivery and detection optical fibers as illustrated in FIG. 1B provides for deeper optical sensing within bone region 110, the optical sensing depth being in-part dependent on the lateral separation of distal ends of the sensing and delivery optical fibers 105.

FIG. 1A and FIG. 1B are both examples of an orthopedic pin wherein reduced-diameter portion 106 includes a second circular outer cross section that is arranged coaxially with the circular outer cross section having the first diameter D1, and wherein the second circular outer cross section has a second diameter that is less than first diameter D1.

Figure 2A:
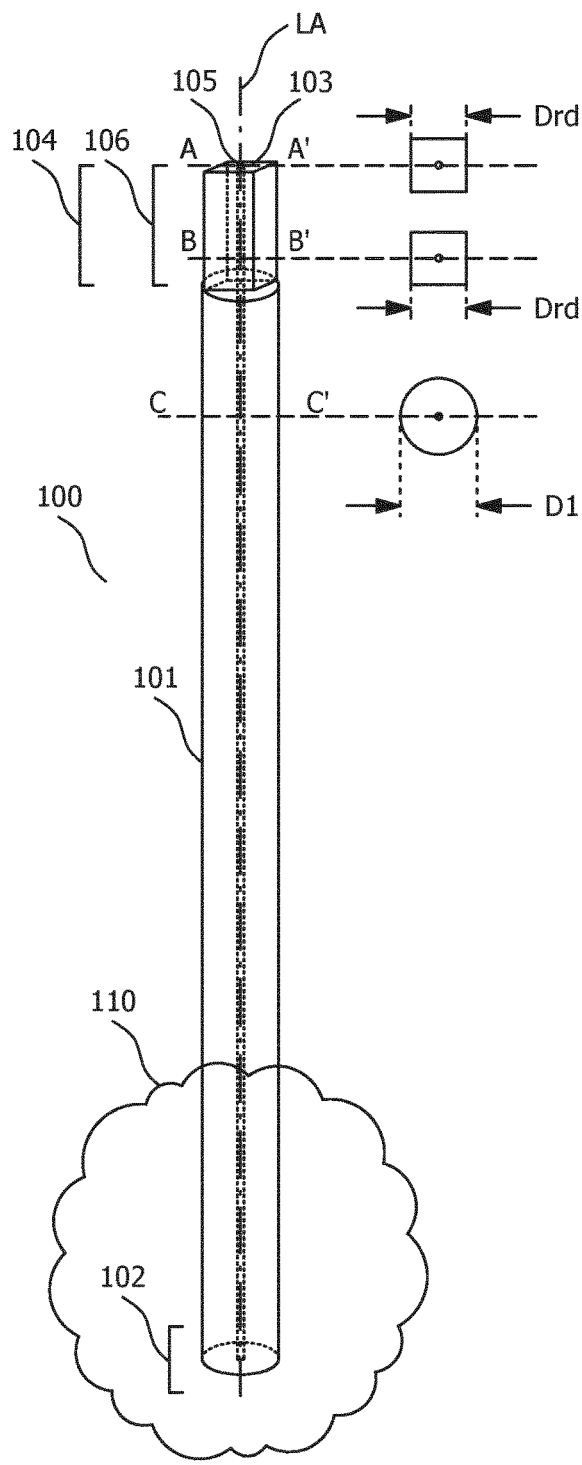
FIG. 2A illustrates an orthopedic pin 100 for optically analyzing a bone region 110 and wherein reduced-diameter portion 106 includes a rectangular cross section.
Figure 2B:
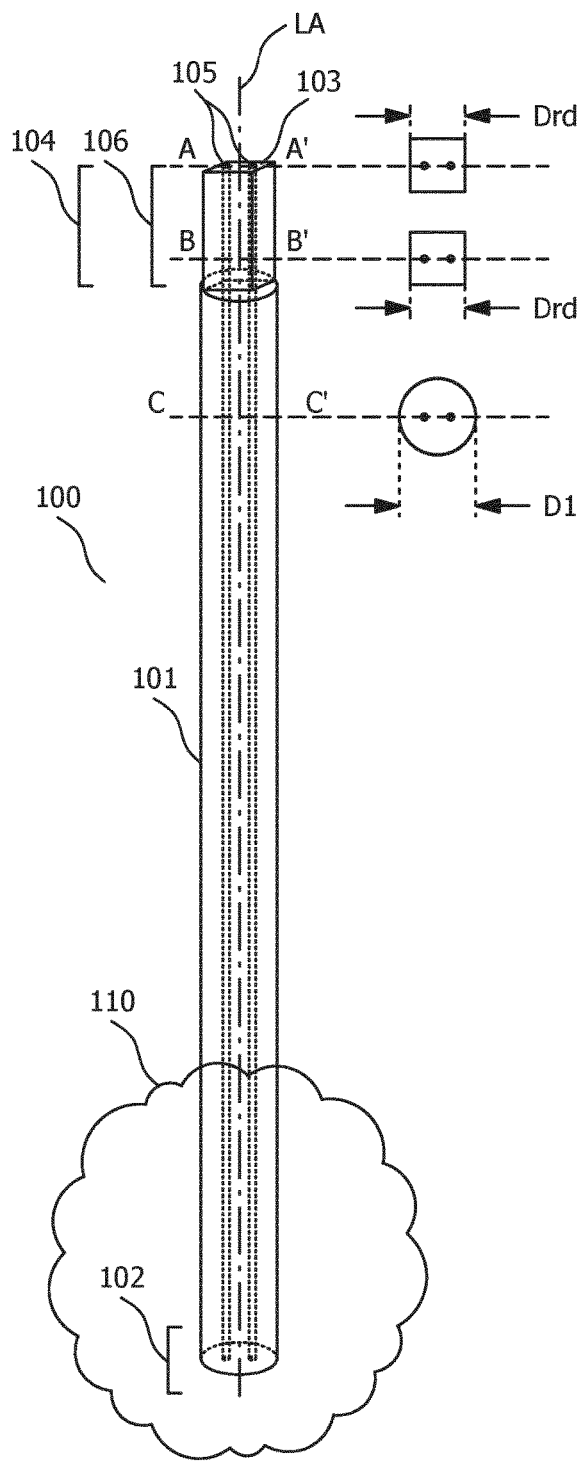
FIG. 2B illustrates an orthopedic pin 100 having two optical fibers 105 for optically analyzing a bone region 110 and wherein reduced-diameter portion 106 includes a rectangular cross section.
Figure 3A:
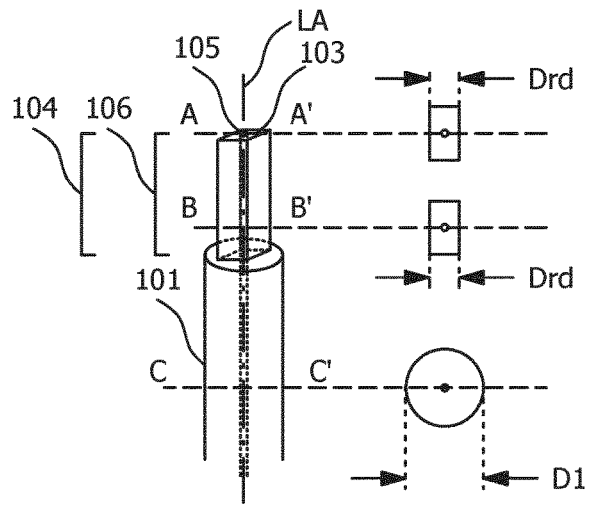
FIG. 3A-3F each illustrate an optical connector portion 104 of an orthopedic pin 100 having a reduced-diameter portion 106 with an exemplary cross section in a plane perpendicular too longitudinal axis LA.
Figure 3B:
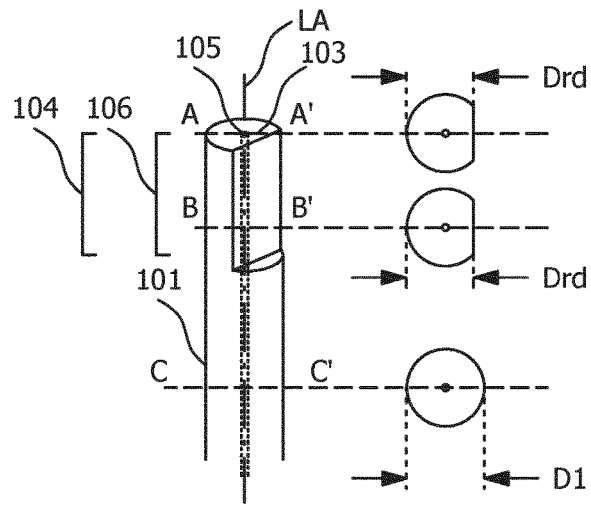
Figure 3C:
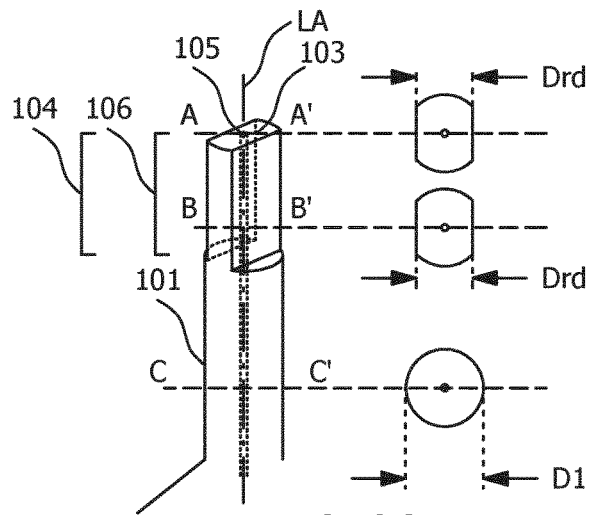
Figure 3D:
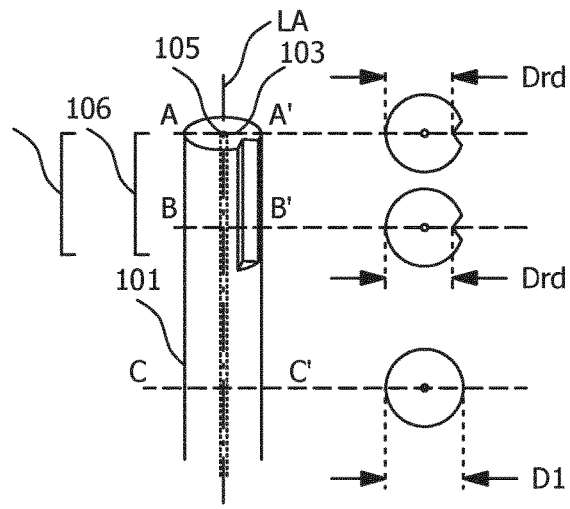
Figure 3E:
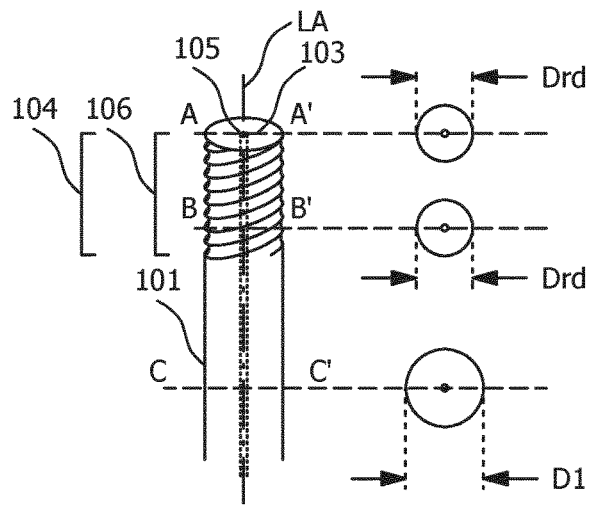
Figure 3F:
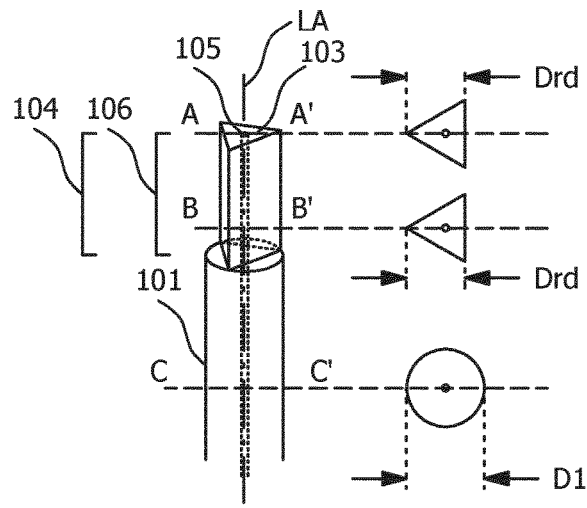
Figure 4:
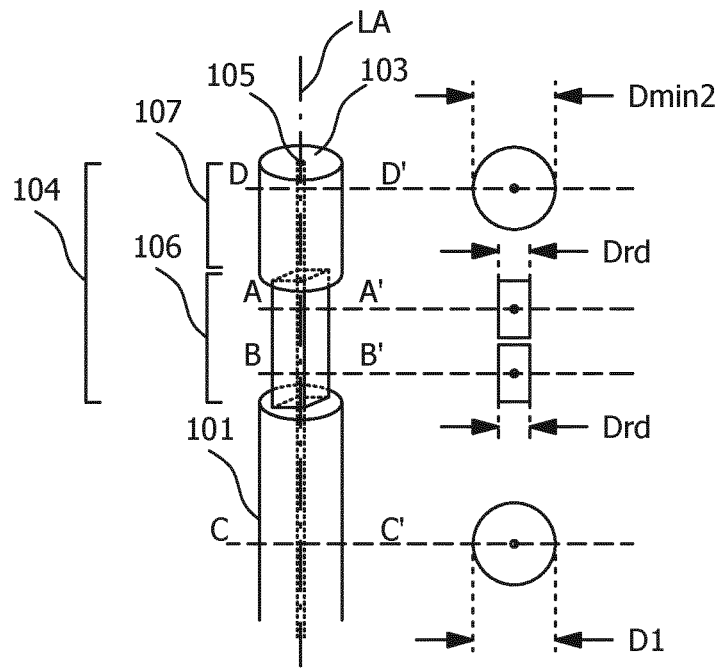
FIG. 4 illustrates an optical connector portion 104 of an orthopedic pin 100 having a reduced-diameter portion 106 which is separated from proximal end 103 by a proximal portion 107 of elongate shaft 101.

Alternative designs to the circular cross sectional profile of reduced-diameter portion 106 in a plane perpendicular to longitudinal axis LA illustrated in FIG. 1 are also contemplated, as illustrated exemplarily in FIGS. 2-4. In some examples, reduced-diameter portion 106 may for example include at least one flat surface extending along the at least a portion of elongate shaft 101. The flat surfaces may provide a gripping surface for gripping orthopedic pin 100, and/or assist in rotationally aligning orthopedic pin 100 with respect to an optical adapter or other counterpart optical connector and thereby releasably mating the orthopedic pin with the optical adapter/counterpart optical connector. Thereto, FIG. 2A illustrates an orthopedic pin 100 for optically analyzing a bone region 110 and wherein reduced-diameter portion 106 includes a rectangular cross section. Thus, the use of four flat surfaces is exemplified in FIG. 2A. As in the FIG. 2A example, the flat surfaces may be arranged in pairs at diametrically opposed positions with respect to longitudinal axis LA of elongate shaft 101. A square cross section is also contemplated. FIG. 2B illustrates an orthopedic pin 100 having two optical fibers 105 for optically analyzing a bone region 110 and wherein reduced-diameter portion 106 includes a rectangular cross section. Except for having two optical fibers, the example of FIG. 2B is identical to that of FIG. 2A. The flat surfaces of FIG. 2B may thus serve to rotationally align the distal ends of optical fibers 105 with counterpart optical fibers, for example in an optical adapter, in order to couple optical radiation therebetween.

FIG. 3A-3F each illustrate an optical connector portion 104 of an orthopedic pin 100 having a reduced-diameter portion 106 with an exemplary cross section in a plane perpendicular to longitudinal axis LA. In FIG. 3A a rectangular cross section is illustrated, in FIG. 3B a single flat surface that forms a chord in the circumference of elongate shaft 101 having diameter D1 is illustrated, in FIG. 3C the use of two flat surfaces arranged as diametrically-opposing chords in the circumference of elongate shaft 101 having diameter D1 is illustrated, in FIG. 3D the use of a notch is illustrated, in FIG. 3E the use of a screw thread is illustrated, and in FIG. 3F the use of three flat surfaces is illustrated. The exemplary orthopedic pins of FIG. 3A-FIG. 3E may have one of more optical fibers 105. Also it is noted that as seen in FIGS. 3B and 3D, the use of an asymmetric cross sectional profile is in general contemplated, in particular for ensuring that there is a only single rotation degree of rotational freedom for aligning orthopedic pin 100 with an optical adapter or a counterpart optical connector; specifically for aligning the optical fiber(s) of orthopedic pin 100 with counterpart optical fibers in the optical adapter/counterpart optical connector in order to couple optical radiation therebetween. The use of various chamfers and bevels and indeed a profile that tapers along the longitudinal axis LA of the examples illustrated herein is also contemplated.

Alternative designs to the optical connector portion 104 at proximal end 103 of orthopedic pin 100 in FIG. 1 are also contemplated. These include providing a proximal portion 107 of elongate shaft 101 between reduced-diameter portion 106 and proximal end 103 for which the diameter in a direction parallel to the width Drd, is increased with respect to Drd and which also does not extend beyond the circular cross sectional profile of elongate shaft 101 as determined by diameter D1. This is illustrated in FIG. 4, which illustrates an optical connector portion 104 of an orthopedic pin 100 having a reduced-diameter portion 106 which is separated from proximal end 103 by a proximal portion 107 of elongate shaft 101. FIG. 4 is an example of an orthopedic pin wherein reduced-diameter portion 106 is separated from the proximal end 103 of elongate shaft 101 by a proximal portion 107 of the elongate shaft 101 having an outer cross section comprising a minimum width Dmin2 perpendicularly with respect to the elongate shaft 101 and parallel to the width Drd of the reduced-diameter portion 106 that exceeds the width Drd of the reduced-diameter portion 106 and is less than or equal to the first diameter D1. Proximal portion 107 may serve to axially support a proximal end of orthopedic pin 100, particularly when a portion of its cross section has a diameter that is equal to the first diameter D1 and when the elongate pin is received within a channel having the same diameter. This may be useful for example in implementations in which orthopedic pin 100 is hammered into bone and distal end 103 is received within a channel of a surgical hammer as described later herein. The use of proximal portion 107 in combination with any of the other cross-sectional profiles of reduced-diameter portion 106 described herein is also contemplated, as well as in combination with two or more optical fibers.

Figure 5:
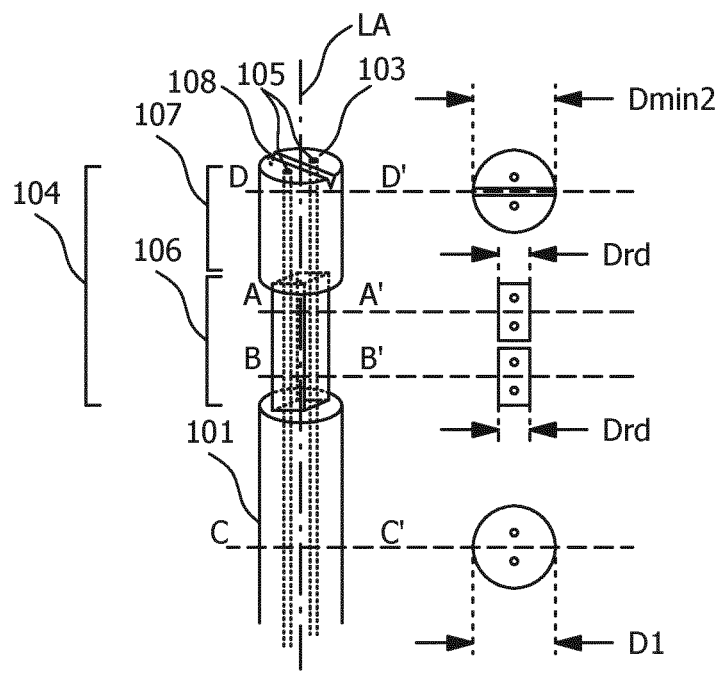
FIG. 5 illustrates an optical connector portion 104 of an orthopedic pin 100 wherein the proximal ends of each of optical fibers 105 are separated by a groove 108.

When two or more optical fibers are included in orthopedic pin 100, it may be beneficial to improve the optical isolation between the proximal enfaces of the optical fibers by including a groove or a ridge or a step between the endfaces of the optical fibers. Thereto, FIG. 5 illustrates an optical connector portion 104 of an orthopedic pin 100 wherein the proximal ends of each of optical fibers 105 are separated by a groove 108. A step or a ridge serves the same purpose. A step may be provided along an axial direction with respect to longitudinal axis LA. Such features act to reduce the waveguiding of optical radiation between the endfaces of the optical fibers which might otherwise lead to errors in the optical analysis. The surface of elongate shaft 101 around each optical fiber 101 may additionally or alternatively be coated in an optically absorbing material in order to further improve the optical isolation. Thus, as exemplified by the groove of FIG. 5, orthopedic pin 100 may include two or more optical fibers 105, each of the two or more optical fibers having a proximal end disposed towards the distal end 103 of elongate shaft 101, and wherein the proximal end of at least one of the two or more optical fibers 105 is separated from the proximal end of at least another of the two or more optical fibers 105 by a groove 108 or a ridge or a step.

It is also to be noted that whilst reduced-diameter portion 106 in FIGS. 1-5 is illustrated as having a constant width Drd along longitudinal axis LA, it is also contemplated to provide alternative cross sections in this portion with a width that varies along longitudinal axis LA and which also comprise a width Drd perpendicularly with respect to the elongate shaft 101, the width Drd being less than the first diameter D1. In this respect reduced-diameter portion 106 may optionally include a taper or one or more undulations such as a zigzag or a corrugated profile, along longitudinal axis LA. Alternatively or additionally reduced diameter portion 106 may include a roughened surface or an array of indentations or protrusions along longitudinal axis LA in order to provide improved grip. These features may thus act in general to improve the releasable mating of the orthopedic pin with a counterpart optical connector such as an optical adapter.

Figure 6A:
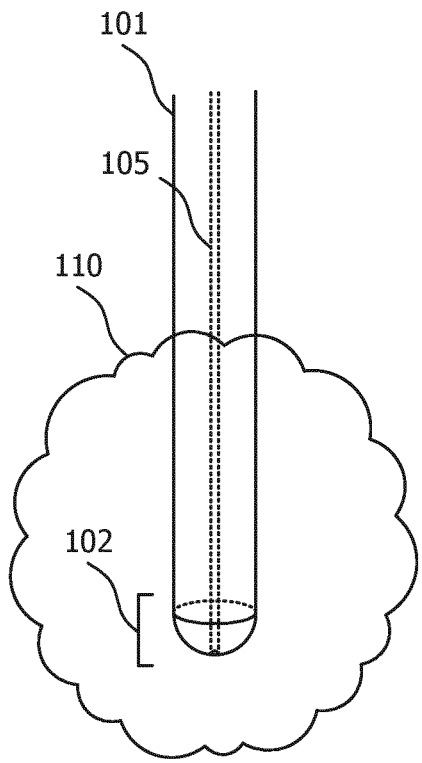
FIG. 6A illustrates an orthopedic pin 100 having distal end 102 with a rounded profile.
Figure 6B:
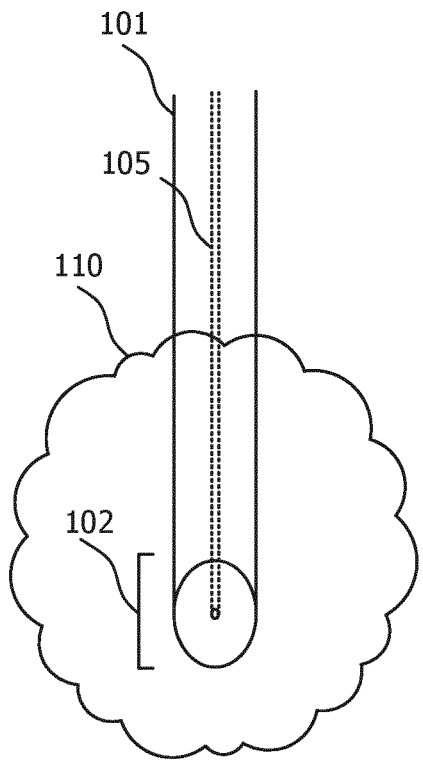
FIG. 6B illustrates an orthopedic pin 100 having distal end 102 with a bevel.

Alternative designs to the distal end 102 of orthopedic pin 100 in FIG. 1 are also contemplated. Distal end 102 may for example have a rounded profile or one or more beveled surfaces in order to improve its ability to penetrate bone. Thereto, FIG. 6A illustrates an orthopedic pin 100 having distal end 102 with a rounded profile, and FIG. 6B illustrates an orthopedic pin 100 having distal end 102 with a bevel.

Figure 7:
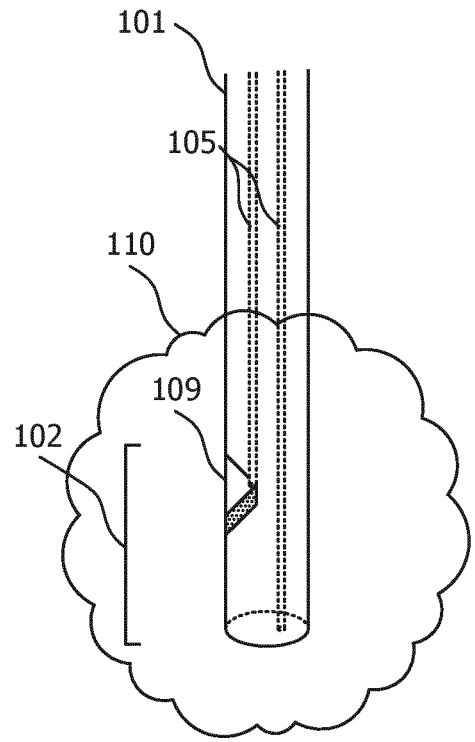
FIG. 7 illustrates a distal end 102 of elongate shaft 101 of an orthopedic pin 100 wherein a distal end of one optical fiber 105 emits and/or receives optical radiation through an opening 109 in elongate shaft and a distal end of another optical fiber 105 emits and/or receives optical radiation through distal end 102 of elongate shaft 101.

When two or more optical fibers are included within orthopedic pin 100, it may be beneficial to perform optical sensing at least in-part along a portion of elongate shaft 101 of orthopedic pin 100. Thereto, FIG. 7 illustrates a distal end 102 of elongate shaft 101 of an orthopedic pin 100 wherein a distal end of one optical fiber 105 emits and/or receives optical radiation through an opening 109 in elongate shaft and a distal end of another optical fiber 105 emits and/or receives optical radiation through distal end 102 of elongate shaft 101. The optical fiber with a distal end closest to the distal end of elongate shaft 101 may be sensitive to and/or emit optical radiation axially with respect to elongate shaft 101. To that purpose its distal end may for example have an endface that this perpendicular, or at a few degrees to its longitudinal axis, or alternatively its distal end may indeed have a rounded profile. The distal end may coincide with the extreme distal end of elongate shaft 101, or for example be disposed in a bevel of said extreme distal end. The other optical fiber in FIG. 7 having a distal end that is proximal to the distal end of the axial sensing/emitting optical fiber may in some implementations be provided with an endface at approximately 45 degrees to its longitudinal axis, and/or include a reflecting or scattering surface for re-directing optical radiation, or providing optical sensitivity, radially with respect to longitudinal axis LA. Opening 109 may be filled with an optically transmitting material, such as a UV-curable optically transparent adhesive, in order to preserve the circular outer cross section of elongate shaft 101 in this region.

The ability to sense/direct optical radiation radially with respect to longitudinal axis LA as exemplified by FIG. 7 has several advantages over disposing optical fibers in axially emitting/sensing positions. When one of the optical fibers 105 illustrated in FIG. 7 is used as a source optical fiber for delivering optical radiation to bone region 110 and the other of the optical fibers is used as a detection optical fiber for receiving optical radiation reflected or scattered by bone region 110, the sensed optical path in bone region 110 forms a curve between the distal ends of the optical fibers. This provides optical sensing of the bone region along a side portion of elongate shaft 101. Moreover, the arrangement of the optical fibers as illustrated may allow for greater separation of their distal ends, increasing the volume of bone region 110 that is optically analyzed. When both optical fibers 105 illustrated in FIG. 7 are arranged for both delivering and sensing optical radiation within bone region 110, independent measurements of the optical properties of bone region 110 may be carried out, thereby providing information on the spatial distribution of the tissue properties—for example one optical fiber may sense the axial proximity of cortical bone and the other optical fiber may sense the lateral proximity of cortical bone. Additional optical fibers may also be incorporated into the arrangement of FIG. 7 and operate in a similar manner.

Thus, orthopedic pin 100 in FIG. 7 includes two optical fibers 105 wherein a distal end of one of the optical fibers 105 emits and/or receives optical radiation through an opening 109 in elongate shaft 101 and in a radial direction with respect to the elongate shaft 101, and wherein a distal end of the other of the optical fibers 105 is emits and/or receives optical radiation through a distal end 102 of the elongate shaft 101 and in an axial direction with respect to the elongate shaft 101.

Figure 8:
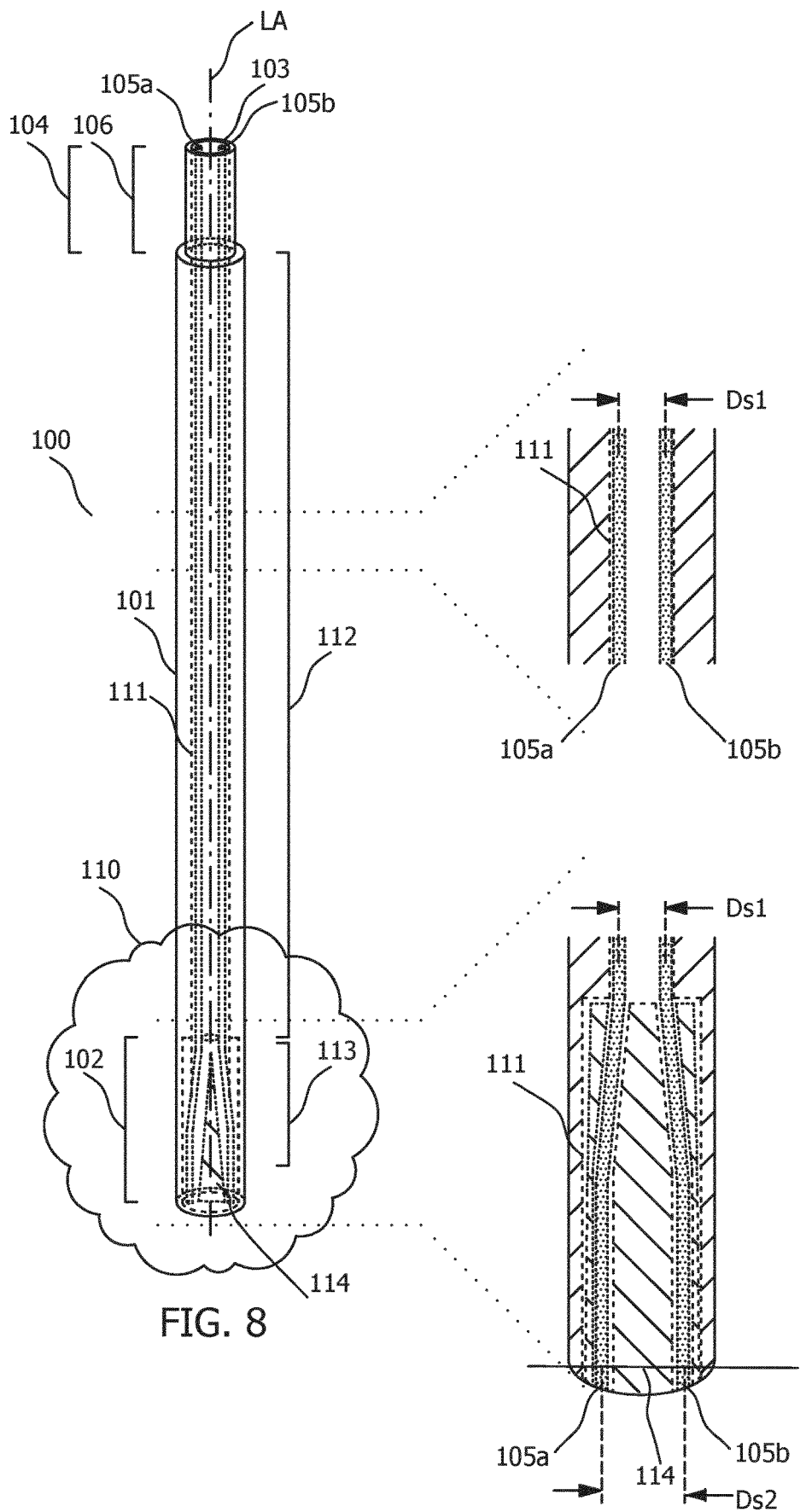
FIG. 8 illustrates an orthopedic pin 100 having a plug 114 that separates a longitudinal axis of a first optical fiber 105a from a longitudinal axis of a second optical fiber 105b.

Alternative designs to the elongate shaft 101 in FIG. 1 are also contemplated. In one implementation, elongate shaft 101 may include a bore 111, a plurality of optical fibers and a plug 114 that fits within the bore. The plug may define a lateral separation distance of the distal ends of the optical fibers. Thereto, FIG. 8 illustrates an orthopedic pin 100 having a plug 114 that separates a longitudinal axis of a first optical fiber 105a from a longitudinal axis of a second optical fiber 105b. With reference to FIG. 8, orthopedic pin 100 includes first optical fiber 105a and second optical fiber 105b. Elongate shaft 101 also includes bore 111 within which first optical fiber 105a and second optical fiber 105b extend. Bore 111 includes a central portion 112 that is disposed between optical connector portion 104 and distal end 102. Within central portion 112 a longitudinal axis of first optical fiber 105a is maximally separated from longitudinal axis of second optical fiber 105b by a first separation distance Ds1. Distal end 102 of elongate shaft 101 includes transition region 113 and plug 114. Bore 111 has a wider diameter in transition region 113 than in central portion 112. Plug 114 fits within bore 111 in transition region 113, and plug 114 separates first optical fiber 105a and second optical fiber 105b such the longitudinal axis of the first optical fiber 105a is separated from the longitudinal axis of the second optical fiber 105b by a second separation distance Ds2. Second separation distance Ds2 is greater than first separation distance Ds1. Transition region 113 and plug 114 may alternatively be included within optical connector portion 104 of elongate shaft 101 in a similar manner in order to provide a predetermined separation between the proximal ends of optical fibers 105a, 105b.

The lateral separation between the distal and/or proximal ends of optical fibers 105a, 105b provided by plug 113 is thus greater than in central portion 112, which allows the use of a thick wall portion of elongate tube 101 in central portion 112—thereby reducing the chance of buckling—and at the same time provides deeper sensing in bone region 110, and/or relaxes the alignment tolerance of coupling proximal end 103 to a corresponding optical connector or adapter. The use of plug 114 may also assist in the manufacturability of orthopedic pin 100 since it provides accurate separation of the distal ends of the optical fibers. As illustrated in FIG. 8, in some implementations an interface between central portion 112 and transition region 113 of bore 111 may include a step, which may be abrupt or optionally include a slope, which step serves to transfer axial shock loads from plug 114 to elongate shaft 101, for example during hammering of orthopedic pin 100, in order to improve penetration in bone region 110. Plug 114 may be formed from the same material as elongate shaft 101, which may for example be a medical grade stainless steel, or from another material, such as a polymer.

Thus, various examples of an orthopedic pin have been described, and it is to be noted that, for the sake of unnecessary duplication, features described in relation to one orthopedic pin may also be used in other orthopedic pins.

Figure 9:
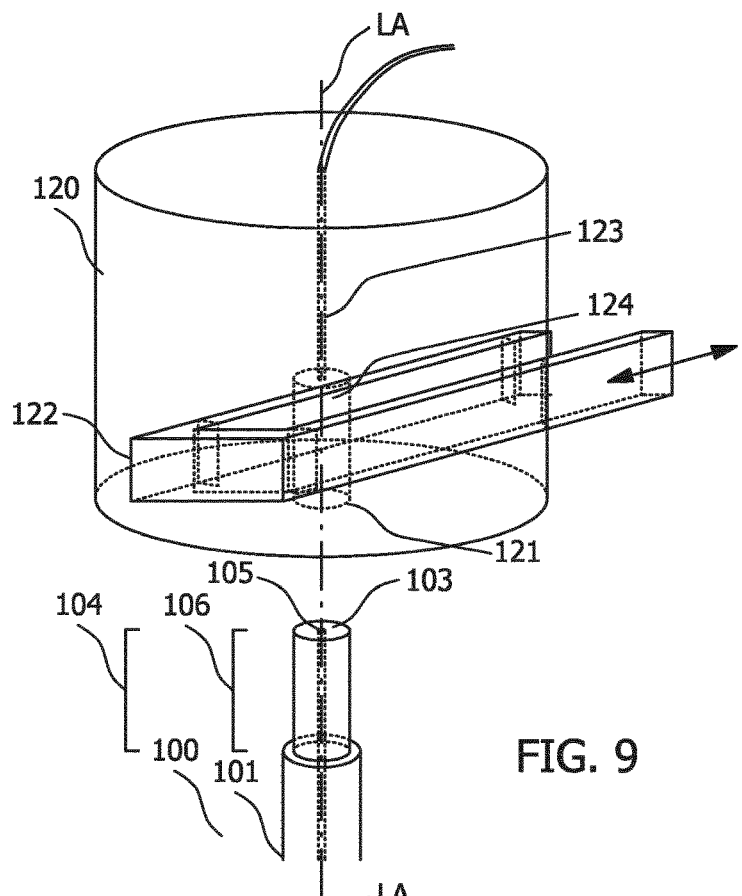
FIG. 9 illustrates an optical adapter 120 for releasably mating with the optical connector portion 104 of orthopedic pin 100.

An optical adapter for releasably mating with the optical connector portion 104 of orthopedic pin 100 is also disclosed. Thereto, FIG. 9 illustrates an optical adapter 120 for releasably mating with the optical connector portion 104 of orthopedic pin 100. The releasable mating provides a convenient means for transferring between a first stage in a surgical procedure during which orthopedic pin 100 is inserted into a bone region and optical sensing is performed by means of an optical coupling to the optical fiber(s) in the orthopedic pin to define a trajectory that does not intercept cortical bone, and a second stage in the surgical procedure during which the inserted orthopedic pin serves as a guide over which a pedicle screw may be inserted by means of a channel in the pedicle screw. In transferring between the first and second stages it is desirable to alleviate the need to remove the orthopedic pin 100 from the bone region, which would otherwise risk losing the desired trajectory. This is facilitated by the aforementioned reduced-diameter portion 106 of the optical connector portion 104, which allows a user to slide the pedicle screw over the distal end of the orthopedic pin.

Various exemplary optical adapters 120 for this purpose are illustrated in FIG. 9-FIG. 14. With reference to FIG. 9, optical adapter 120 includes a port 121, a gripping element 122 and an optical element 123. Port 121 is adapted to receive proximal end 103 of elongate shaft 101 including reduced-diameter portion 106. Optical element 123 is adapted for coupling optical radiation to optical fiber 105. Moreover, when reduced-diameter portion 106 of elongate shaft is received within port 121, gripping element 122 engages with reduced-diameter portion 106 of elongate shaft 101 such that optical element 123 is aligned with optical fiber 105 of orthopedic pin 100 for coupling optical radiation therebetween. Reduced-diameter portion 106 thereby provides a means for releasably mating orthopedic pin 100 with a counterpart optical connector/optical adapter.

In more detail, gripping element 122 includes one or more engaging surfaces 124 for engaging with reduced diameter portion 106 of elongate shaft 101; and in some implementations gripping element 122 is arranged to move, for example slide, transversely with respect to longitudinal axis LA of elongate shaft 101 of orthopedic pin 100 such that when reduced-diameter portion 106 of elongate shaft 101 is received within port 121, engaging surface(s) 124 engage with reduced-diameter portion 106 of elongate shaft 101.

It is noted that one of more additional optical fibers in orthopedic pin 100 and corresponding optical elements 123 in optical adapters 120 may be included in the example of FIG. 9 in a similar manner. Port 121 may be sized in order to receive proximal end 103 of elongate shaft 101. Gripping element 122 is exemplified in FIG. 9 as having a U-shape and may, as illustrated by the arrows, be arranged to slide transversely with respect to longitudinal axis LA in FIG. 9. Upon sliding transversely, frictional resistance between one or more engaging surfaces 124 of gripping element 122, which engaging surfaces in this particular example face one another and are arranged on inwardly facing portions of the U-shape, and optical connector portion 104, acts to retain orthopedic pin 100 in optical adapter 100. Engaging surface(s) 124 of gripping element 122 may optionally be roughened or include an array of indentations or protrusions along longitudinal axis LA in order to provide improved grip. These features may improve the releasable mating of the orthopedic pin with the optical adapter.

In order to improve the retention of orthopedic pin 100 in optical adapter 100, gripping element 122 and/or a portion of body of adapter 120, may additionally include a wedge-shaped profile arranged so as to pinch portions of optical connector portion 104 when gripping element 122 is slid transversely with respect to longitudinal axis LA.

In an alternative implementation, rather than having a U-shape, gripping element 122 in FIG. 9 may include only a single elongate member, optionally together with the aforementioned wedge(s) that upon being slid transversely with respect to longitudinal axis LA, likewise engages with optical connector portion 104, for example by pinching one side of optical connector portion 104 against a fixed surface provided within the body of optical adapter 120. Various other forms of gripping element 122 are described below.

Optical element 123 in FIG. 9 may be provided by an optical fiber, as illustrated, or by another optical waveguide in a similar manner. The use of one or more lenses (not illustrated) in coupling optical radiation between optical element 123 and a distal end of optical fiber(s) 105 of orthopedic pin 100 is also contemplated. Such lens(es) may help to relax the alignment tolerance between optical element 123 and the optical fiber(s), for example by over-filling the distal end(s) of the optical fiber(s) with optical radiation. Optical element 123 may provide an optical connection to an optical source and/or detector (not illustrated), which may be separate to the optical adapter, for example in the form of a console, or both optical adapter 120 and an optical source and/or detector may be integrated into a handheld surgical tool as described hereinbelow. In the above separate arrangement, the optical fiber(s) serving as optical element 123 may for example have a length of 1 meter or more.

Figure 10:
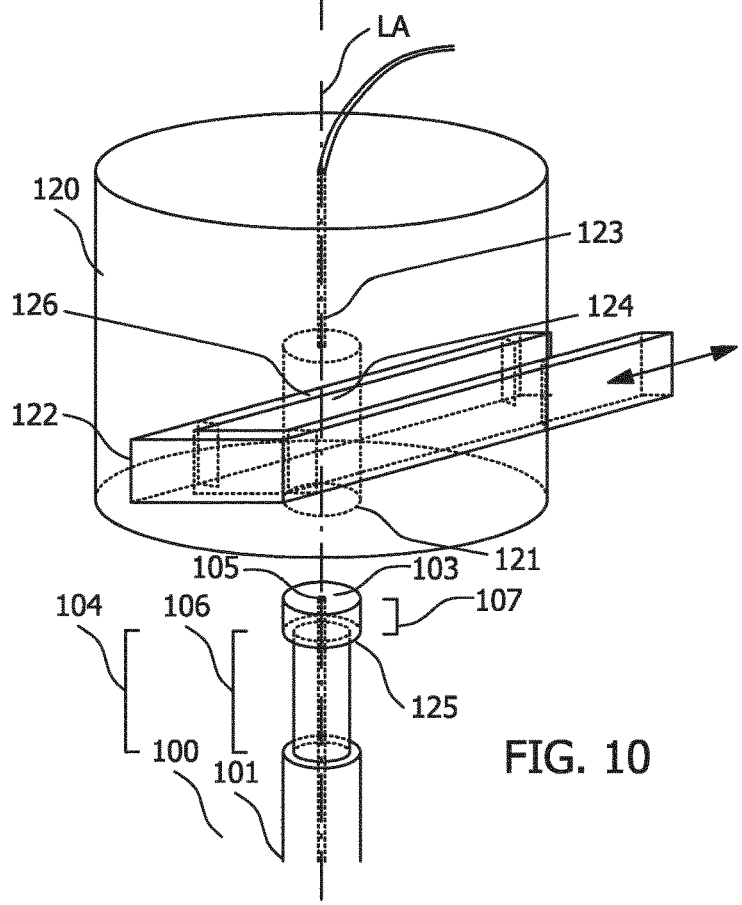
FIG. 10 illustrates an optical adapter 120 for releasably mating with the optical connector portion 104 of orthopedic pin 100 wherein reduced-diameter portion 106 is separated from proximal end 103 by a proximal portion 107.

FIG. 10 illustrates an optical adapter 120 for releasably mating with the optical connector portion 104 of orthopedic pin 100 wherein reduced-diameter portion 106 is separated from proximal end 103 by a proximal portion 107. The optical adapter of FIG. 10 differs from that of FIG. 9 in that port 121 is adapted to receive proximal portion 121 as well as reduced-diameter portion 106 of elongate shaft 101. In FIG. 10, reduced-diameter portion 106 of elongate shaft of orthopedic pin 100 is separated from proximal end 103 of elongate shaft 101 by proximal portion 107 of elongate shaft 101 having an outer cross section with a minimum width Dmin2 perpendicularly with respect to elongate shaft 101 and parallel to the width Drd of reduced-diameter portion 106. Minimum width Dmin2 of proximal portion 107 exceeds width Drd of reduced-diameter portion 106, and is less than or equal to first diameter D1. Moreover, a transition between reduced diameter portion 106 and proximal portion 107 provides a step 125 for retaining orthopedic pin 100 in port 121. Gripping element 122 also includes a corresponding surface 126 for engaging with step 125 when reduced-diameter portion 106 of elongate shaft 101 is received within port 121 such that the orthopedic pin 100 is retained in port 121. The transition between reduced diameter portion 106 and proximal portion 107 thus serves to improve the retention of orthopedic pin 100 in port 121.

Figure 11:
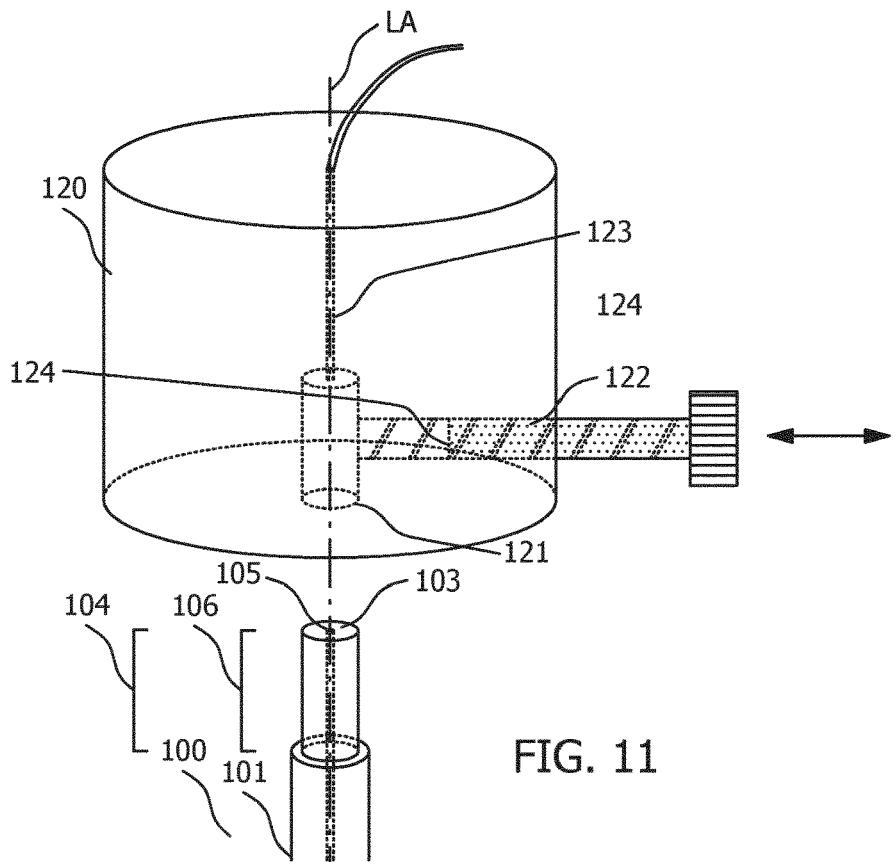
FIG. 11 illustrates an optical adapter 120 having a gripping element 122 in the form of a threaded screw.

FIG. 11 illustrates an optical adapter 120 having a gripping element 122 in the form of a threaded screw. As in FIG. 9, gripping element 122 in FIG. 11 is configured to move transversely, as indicated by the arrows, with respect to longitudinal axis LA in order to engage reduced-diameter portion 106 of elongate shaft 101. The example of FIG. 11 differs from FIG. 9 in that instead of gripping element 122 moving transversely with respect to a longitudinal axis LA of elongate shaft 101 by sliding transversely with respect to the longitudinal axis LA, a threaded screw serves as gripping element 122 and the threaded screw moves transversely with respect to the longitudinal axis LA of the elongate shaft 101 by rotating in a plane parallel to the longitudinal axis LA.

Figure 12:
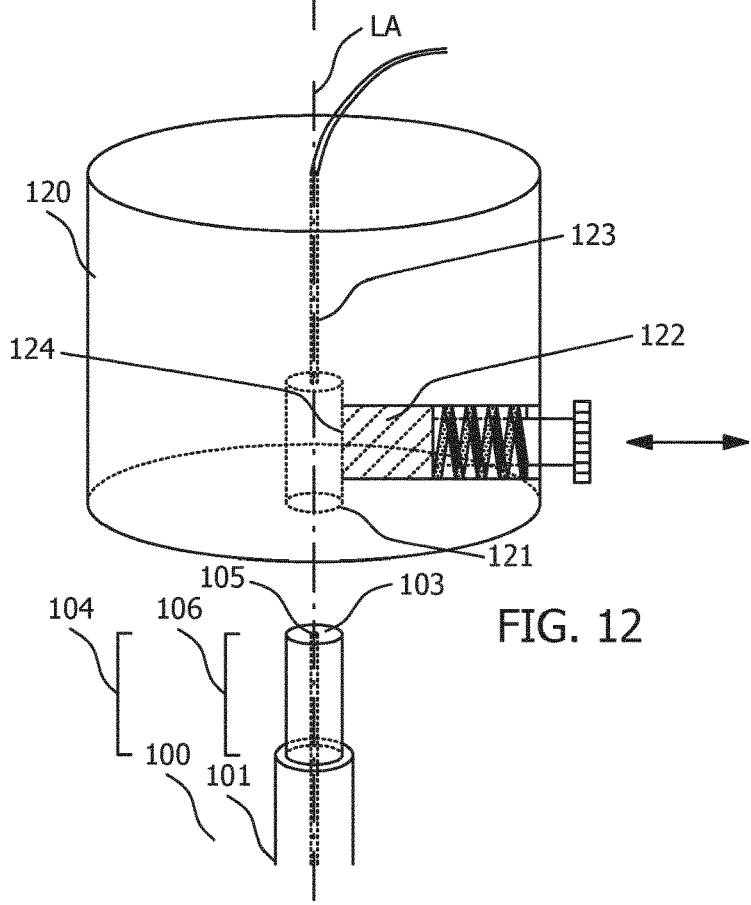
FIG. 12 illustrates an optical adapter 120 having a gripping element 122 in the form of a spring-loaded piston.

FIG. 12 illustrates an optical adapter 120 having a gripping element 122 in the form of a spring-loaded piston. As in FIG. 9, gripping element 122 in FIG. 12 is configured to move transversely, and by sliding, as indicated by the arrows, with respect to longitudinal axis LA in order to engage reduced-diameter portion 106 of elongate shaft 101. The example of FIG. 12 differs from FIG. 9 in that a spring-loaded piston serves as gripping element 122.

Figure 13:
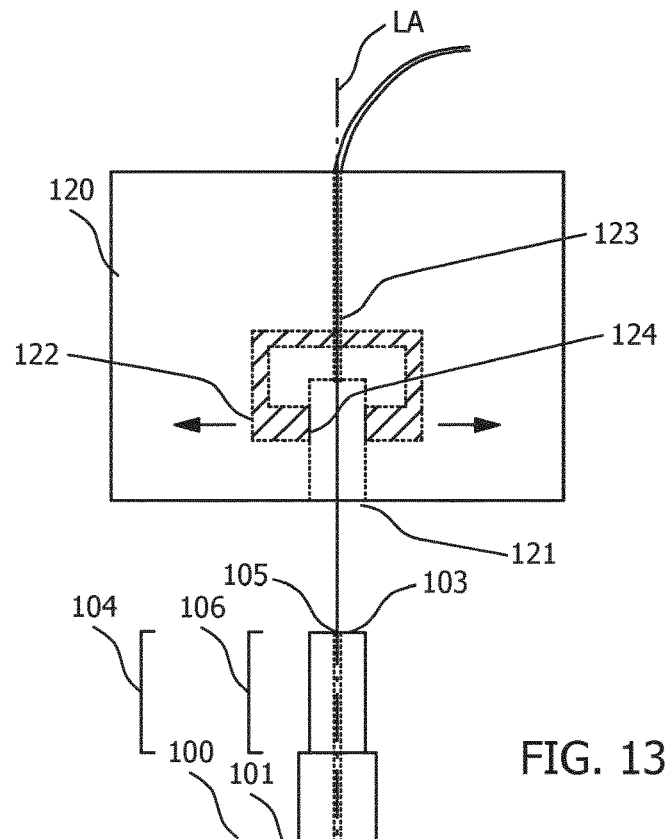
FIG. 13 illustrates a cross section of an optical adapter 120 having a gripping element 122 in the form of a pair of spring-loaded jaws.

FIG. 13 illustrates a cross section of an optical adapter 120 having a gripping element 122 in the form of a pair of spring-loaded jaws. As with the gripping element in FIG. 9, the spring-loaded jaws in FIG. 12 are configured to move transversely, as indicated by the arrows, with respect to longitudinal axis LA in order to engage reduced-diameter portion 106 of elongate shaft 101. The example of FIG. 12 differs from FIG. 9 in that spring-loaded jaws serve as gripping element 122. A single jaw may alternatively be used in a similar manner.

Figure 14:
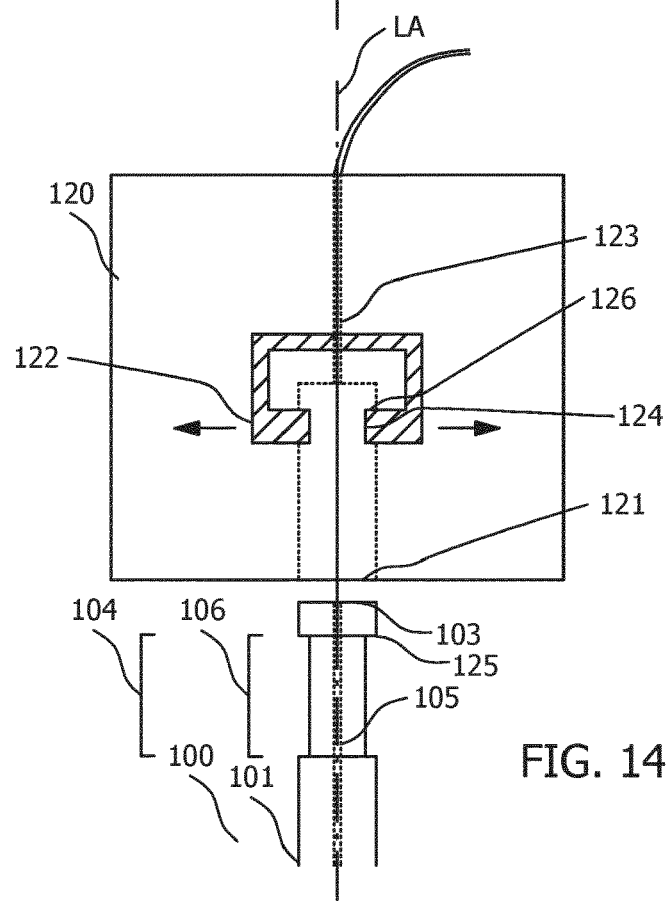
FIG. 14 illustrates a cross section of an optical adapter 120 having a gripping element 122 in the form of a pair of spring-loaded jaws for releasably mating with the optical connector portion 104 of an orthopedic pin 100 wherein the reduced-diameter portion 106 is separated from proximal end 103 by a proximal portion 107.

FIG. 14 illustrates a cross section of an optical adapter 120 having a gripping element 122 in the form of a pair of spring-loaded jaws for releasably mating with the optical connector portion 104 of an orthopedic pin 100 wherein the reduced-diameter portion 106 is separated from proximal end 103 by a proximal portion 107. The optical adapter of FIG. 14 differs from that of FIG. 13 in that port 121 is adapted to receive proximal portion 121 as well as reduced-diameter portion 106 of elongate shaft 101. Again, a single jaw may alternatively be used in a similar manner.

Thus, various examples of an optical adapter have been described, and it is to be noted that, for the sake of unnecessary duplication, features described in relation to one optical adapter may also be used in other adapters.

Figure 15:
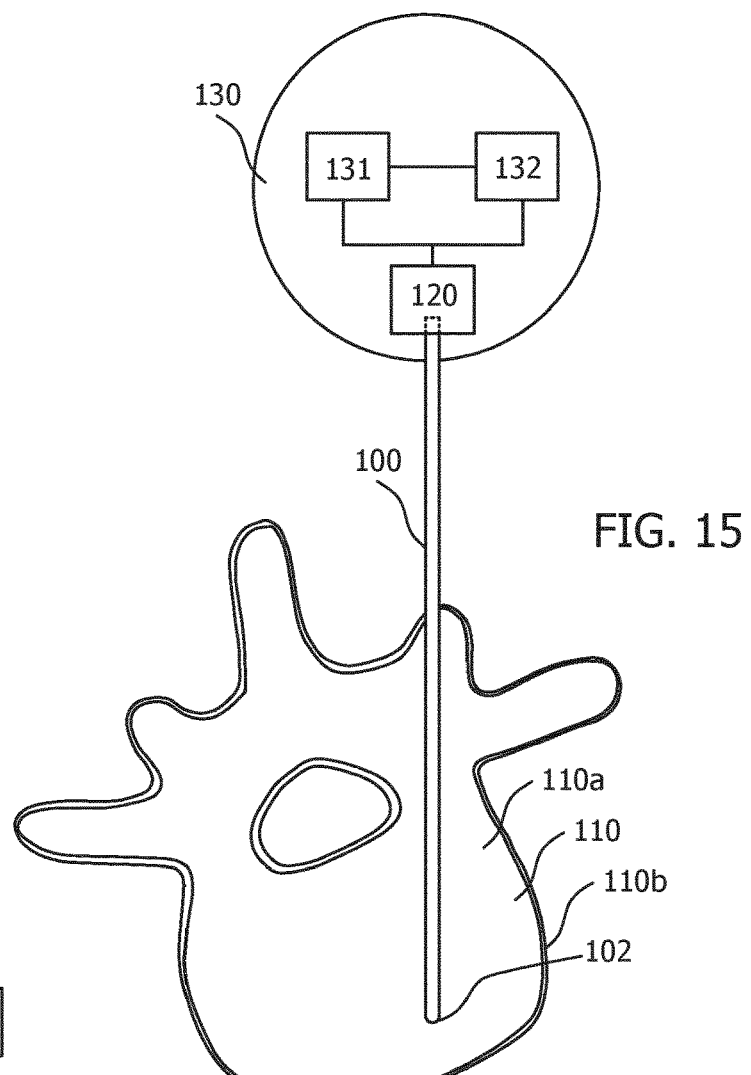
FIG. 15 illustrates a handheld surgical tool 130 in the form of an awl comprising an optical adapter 120, a spectrometer 131 and a processor 132.

The above-described optical adapter may also be included in a handheld surgical tool, such as an awl, a drill, or a screwdriver or a hammer. Thereto, FIG. 15 illustrates a handheld surgical tool 130 in the form of an awl comprising an optical adapter 120, a spectrometer 131 and a processor 132. Handheld surgical tool 130 includes optical adapter 120, a spectrometer 131, and a processor 132, these units being interconnected as illustrated by the interconnecting lines in FIG. 15. Spectrometer 131 includes at least one optical source (not illustrated) and at least one optical detector (not illustrated). The at least one optical source and the at least one optical detector are optically coupled to the at least one optical element 123 of the optical adapter 120 and arranged such that when an orthopedic pin 100 is received within port 121 of optical adapter 120, and when the distal end 102 of the elongate shaft 101 of orthopedic pin 100 is inserted into bone region 110, optical radiation generated by the at least one optical source irradiates bone region 110 via the at least one optical fiber 105, and optical radiation reflected or scattered by the bone region 110 is optically coupled to the at least one optical detector via the at least one optical fiber 105. Processor 132 is in communication with spectrometer 131 and is configured to perform the following method steps, which are indicated further in FIG. 16:

cause S1 the optical source to generate the optical radiation for optically irradiating the bone region 110;

receive S2 electrical signals generated by the at least one optical detector in response to optically irradiating the bone region 110;

process S3 the received electrical signals with an algorithm configured to:
determine S4 at least a first parameter indicative of a fat content or a water content in the bone region 110 based on the received electrical signals; and to
identify S5 a type of the bone region 110 based on the at least a first parameter; the type being at least one of cancellous bone and cortical bone.

Figure 16:
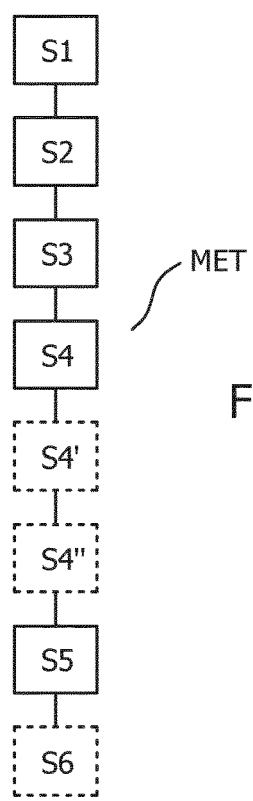
FIG. 16 illustrates a flowchart of a method MET that may be executed by processor 132 of a handheld surgical tool 130.

In this respect, FIG. 16 illustrates a flowchart of a method MET that may be executed by processor 132 of a handheld surgical tool 130.

Optionally the algorithm may be further configured to:
determine S4' at least a second parameter indicative of a collagen content and/or optical scattering in the bone region 110; and to
identify S5 the type of the bone region 110 based further on the at least a second parameter.

The inclusion of collagen and/or optical scattering in the analysis may further improve the discrimination between cortical bone and cancellous bone.

Moreover, the algorithm may be further configured to:
determine S4" a blood content in the bone region 110.

The surgical tool may further comprise an indicator; wherein the indicator is configured to generate S6:
a first output if the type of the bone region 110 is cancellous bone 110a;
a second output if the type of the bone region 110 is cortical bone 110b;
a third output indicative of a certainty of the identification of the type of the bone region 110, the third output being provided based on the determined blood content in the bone region 110.

The certainty of the identification of the type of the bone region has been found to inversely correlate with blood content. This is because if the orthopedic pin is inserted into a bone region and then withdrawn slightly, the resulting void between the distal end of the orthopedic pin and the bone region tends to be filled with blood. The optical signal may be unreliable due to the absence of contact between the distal end and the bone region. Thus, if blood is detected in the optical signal it may be indicative of an unreliable signal.

A technique for optically analyzing the bone region 110 based on optical radiation diffusely reflected from the bone region in order to determine the aforementioned optical parameters as delivered by optical fiber(s) 105 is described in a document by R. Nachabé, B. H. W. Hendriks, M. V. D. Voort, A. E, and H. J. C. M. Sterenborg, "*Estimation of biological chromophores using diffuse optical spectroscopy: benefit of extending the UV-VIS wavelength range to include 1000 to 1600 nm*", Optics Express, vol. 18, 2010, pp. 879-888, and a document by R. Nachabe, B. H. W. Hendriks, A. E. Desjardins, M. van der Voort, M. B. van der Mark, and H. J. C. M. Sterenborg, "*Estimation of lipid and water concentrations in scattering media with diffuse optical spectroscopy from 900 to 1600 nm*", Journal of Biomedical Optics, vol. 15, May. 2010, pp. 037015-10. From these diffuse reflectance spectroscopy, i.e. DRS, measurements, tissue transitions can be deduced, wherein furthermore specifically a parameter indicative of a fat content of the tissue can be obtained.

Although diffuse reflectance spectroscopy is described above to extract tissue properties, other optical methods can also be envisioned, including diffuse optical tomography by employing a plurality of optical fibers, differential path length spectroscopy, fluorescence and Raman spectroscopy. Additionally, acquisition of optical data could be done via a probe that is contact with the tissue or via a non-contact probe.

In order to determine whether a certain tissue is in front of the optical fiber(s), the DRS signal can be compared with a look-up-table. Another way is to translate the measured parameters into physiological parameters and define ranges for these parameters for each tissue type. Incorporating referral is made to Duck, F. A., "*Physical properties of tissue: A comprehensive reference book*", 1990, Academic Press, Harcourt Brace Jovanovich, Publishers, where methods based on classification and regression tree "CART" analyses are described for classifying tissue based on these physiological parameters.

An example of extracting the physiological parameter is by fitting the acquired spectra using a custom made Matlab 7.9.0, Mathworks, Natick, MA, algorithm. In this algorithm, a widely accepted analytical model was implemented, namely the model introduced by T. J. Farrel, M. S. Patterson and B. C. Wilson, "*A diffusion theory model of spatially resolved, steady-state diffuse reflectance for the non-invasive determination of tissue optical properties*", Med. Phys. 19 (1992) p. 879-888. The input arguments for the model of Farrel et al. are the absorption coefficient $\mu_a(\lambda)$, the reduced scattering coefficient $\mu_s'(\lambda)$ and the center-to-center distance between the emitting and collecting fibers at the tip of the probe. For a complete description of the diffusion theory model, referral is made to the document of Farrel et al.

In the following, the model will be explained briefly. The formulas are mainly based on the work of Nachabé et al. mentioned above (R. Nachabé, B. H. W. Hendriks, M. V. D. Voort, A. E, and H. J. C. M. Sterenborg, "*Estimation of biological chromophores using diffuse optical spectroscopy: benefit of extending the UV-VIS wavelength range to include 1000 to 1600 nm*", Optics Express, vol. 18, 2010, pp. 879-888, and furthermore reference is made in this context also to R. Nachabe, B. H. W. Hendriks, A. E. Desjardins, M. van der Voort, M. B. van der Mark, and H. J. C. M. Sterenborg, "*Estimation of lipid and water concentrations in scattering media with diffuse optical spectroscopy from 900 to 1600 nm*", Journal of Biomedical Optics, vol. 15, May. 2010, pp. 037015-10.

A double power law function can be used to describe the wavelength dependence of the reduced scattering coefficient, where the wavelength $\lambda$ is expressed in nm and is normalized to a wavelength value of $\lambda_0=800$ nm. The parameter a corresponds to the reduced scattering amplitude at this specific wavelength.

$$\mu_s'(\lambda) = a\left(\rho_{MR}\left(\frac{\lambda}{\lambda_0}\right)^{-b} + (1-\rho_{MR})\left(\frac{\lambda}{\lambda_0}\right)^{-4}\right) \text{ [cm}^{-1}\text{]} \quad \text{(Eq. 1)}$$

In this equation the reduced scattering coefficient is expressed as the sum of Mie and Rayleigh scattering where pin is the Mie-to-total reduced scattering fraction. The reduced scattering slope of the Mie scattering is denoted as b and is related to the particle size.

Figure 17:
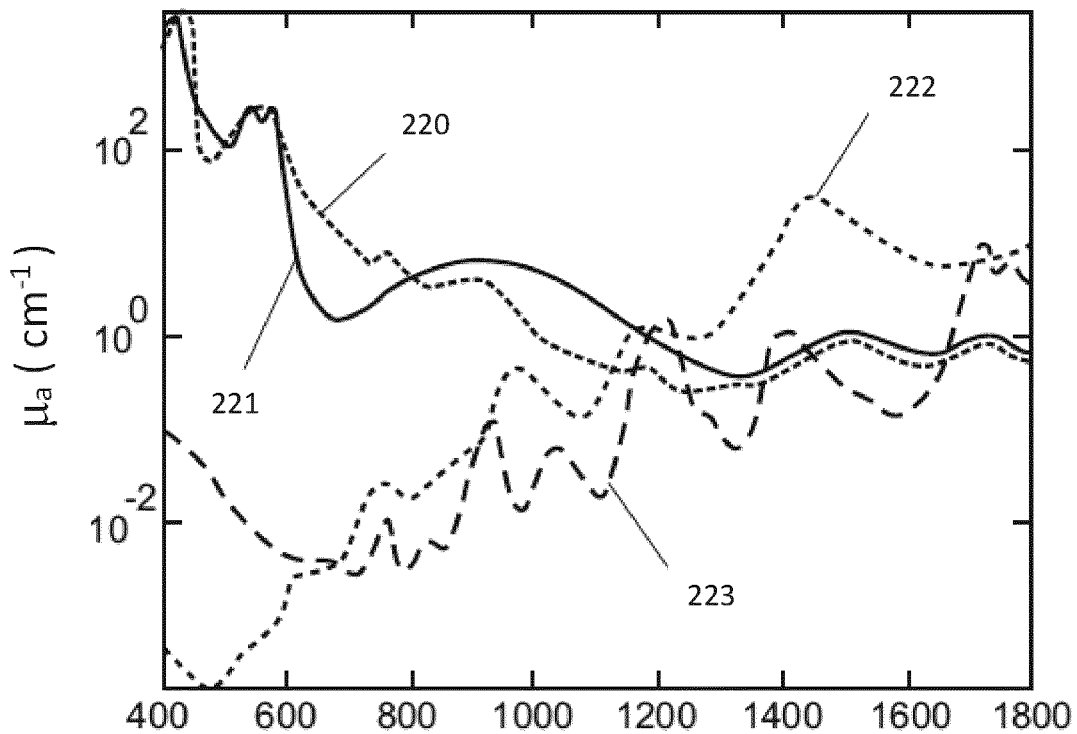
FIG. 17 illustrates a log plot of the absorption spectra of blood hemoglobin (line 220), oxygenated hemoglobin (line 221), water (line 222) and fat (line 223), with the abscissa indicating the wavelength in nm and the ordinate showing $\mu_a(\lambda)$ in $cm^{-1}$.

For a homogeneous distribution of absorbers, the total light absorption coefficient $\mu_a(\lambda)$ can be computed as products of the extinction coefficients and volume fraction of the absorbers (see FIG. 17, which illustrates a log plot of the absorption spectra of blood hemoglobin (line 220), oxygenated hemoglobin (line 221), water (line 222) and fat (line 223), with the abscissa indicating the wavelength in nm and the ordinate showing $\mu_a(\lambda)$ in cm$^{-1}$):

$$\mu_a^{Total} = f_1\mu_a^1 + f_2\mu_a^2 + f_3\mu_a^3 + \ldots \quad \text{(Eq. 2)}$$

Instead of modeling the absorption coefficient $\mu_a(\lambda)$ as the sum of absorption coefficients weighted by the respective concentrations of the four chromophores of interest, it was decided to express the tissue absorption coefficient as $$\mu_a^{Tissue}(\lambda) = C(\lambda)v_{Blood}\mu_a^{Blood}(\lambda) + v_{WL}\mu_a^{WL}(\lambda) \text{ [cm}^{-1}\text{]} \quad \text{(Eq. 3)}$$

where $\mu_a^{Blood}(\lambda)$ corresponds to the absorption by blood and $\mu_a^{WL}(\lambda)$ corresponds to absorption by water and lipid together in the probed volume. The volume fraction of water and lipid is $v_{WL}=[\text{Lipid}]+[\text{H}_2\text{O}]$, whereas $v_{Blood}$ represents the blood volume fraction for a concentration of hemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as:

$$C(\lambda) = \frac{1 - \exp(-2R\mu_a^{Blood}(\lambda))}{2R\mu_a^{Blood}(\lambda)} \quad \text{(Eq. 4)}$$

where R denotes the average vessel radius expressed in cm. The absorption coefficient related to blood is given by:

$$\mu_a^{Blood}(\lambda) = \alpha_{BL}\mu_a^{HbO_2}(\lambda) + (1-\alpha_{BL})\mu_a^{Hb}(\lambda) \text{ [cm}^{-1}\text{]} \quad \text{(Eq. 5)}$$

where $\mu_a^{HbO_2}(\lambda)$ and $\mu_a^{Hb}(\lambda)$ represent the basic extinction coefficient spectra of oxygenated hemoglobin HbO$_2$ and deoxygenated hemoglobin Hb, respectively. The oxygenated hemoglobin fraction in the total amount of hemoglobin is noted as $\alpha_{BL}=[\text{HbO}_2]/([\text{HbO}_2]+[\text{Hb}])$ and is commonly known as the blood oxygen saturation. The absorption due to the presence of water and lipid in the measured tissue is defined as:

$$\mu_a^{WL}(\lambda) = \alpha_{WL}\mu_a^{Lipid}(\lambda) + (1-\alpha_{WL})\mu_a^{H_2O}(\lambda) \text{ [cm}^{-1}\text{]} \quad \text{(Eq. 6)}$$

In this case the concentration of lipid related to the total concentration of lipid and water together can be written as $\alpha_{WF}=[\text{Lipid}]/([\text{Lipid}]+[\text{H}_2\text{O}])$, where [Lipid] and [H$_2$O] correspond to the concentration of lipid (density of 0.86 g/ml) and water, respectively.

This way of relating the water and lipid parameters in the expression of the absorption coefficient is defined in Eq. 6, rather than estimating separately the water and lipid volume fraction corresponding to a minimization of the covariance of the basic functions for fitting, thus resulting in a more stable fit (see, also for further explanation and validation of this theorem the above mentioned papers by R. Nachabé et al.).

Other optical absorbers could also be incorporated into this algorithm, such as: lycopene, vitamin A, β-carotene, or bile.

Another way to discriminate differences in spectra is by making use of a principal component analysis. This method allows classification of differences in spectra and thus allows discrimination between tissues. It is also possible to extract features from the spectra.

Figure 18:
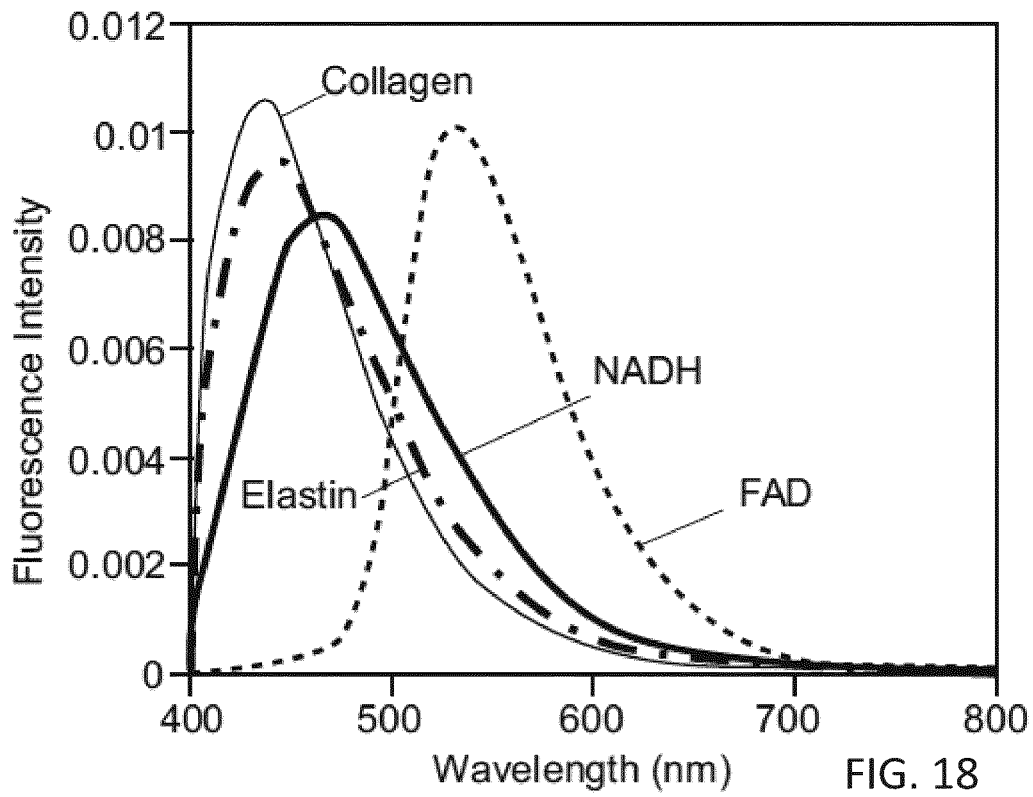
FIG. 18 illustrates intrinsic fluorescence curves for collagen, elastin, NADH and FAD, with the abscissa providing the wavelength in nm and the ordinate giving the fluorescence intensity in arbitrary units.

Aside from diffuse reflectance one could also measure fluorescence spectra. Then for instance parameters like collagen, elastin, Nicotinamide adenine dinucleotide in reduced form, i.e. NADH, and Flavin adenine dinucleotide, i.e. FAD could also be measured (see FIG. 18, which illustrates intrinsic fluorescence curves for collagen, elastin, NADH and FAD, with the abscissa providing the wavelength in nm and the ordinate giving the fluorescence intensity in arbitrary units. The ratio NADH/FAD, which is called the optical redox parameter, is of interest because it is an indicator for the metabolic state of the tissue (see M. Müller and B. H. W. Hendriks, "*Recovering intrinsic fluorescence by Monte Carlo modeling*", J. Biomed. Optics vol. 18 (2013) p. 027009-1 to 027009-13, and references therein, which can also be used to discriminate tissues.

It is noted that any of the method steps disclosed herein, particularly those described in relation to processor 132, may be recorded in the form of instructions which when executed on the processor cause the processor to carry out such method steps.

The instructions may be stored on a computer program product. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

Figure 19:
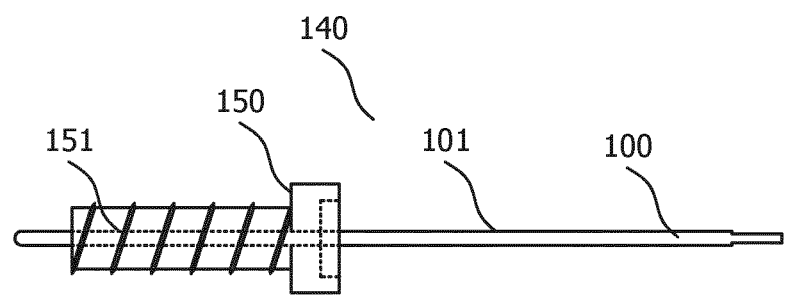
FIG. 19 illustrates a kit 140 including an orthopedic pin 100 received within a channel 151 of a pedicle screw 150.
Figure 20:
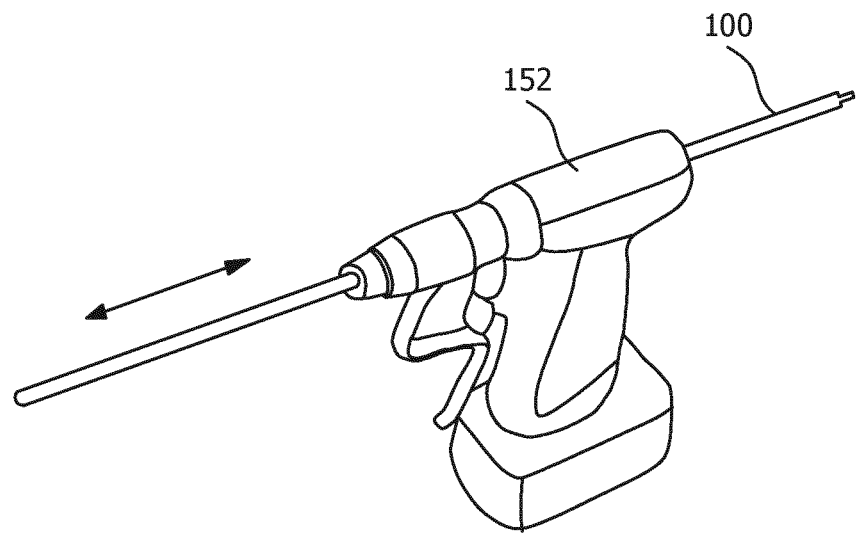
FIG. 20 illustrates another kit 140 including an orthopedic pin 100 received within a channel of a surgical hammer 152.

The orthopedic pin described herein may be provided as part of a kit that includes a surgical device. In one example a kit may include an orthopedic pin and a pedicle screw 150, wherein the pedicle screw comprises a channel 151 for receiving the elongate shaft 101 of the orthopedic pin 100. In another example a kit may include an orthopedic pin and a hollow drill having a channel configured to receive the orthopedic pin. In another example a kit may include an orthopedic pin and a surgical screwdriver having a channel configured to receive the orthopedic pin. In another example a kit may include an orthopedic pin and a surgical hammer 152 having a channel 151 configured to receive the orthopedic pin 100. The provision of an orthopedic pin with a surgical tool that combines hammering and drilling and screwing functions is also contemplated. Thereto, FIG. 19 illustrates a kit 140 including an orthopedic pin 100 received within a channel 151 of a pedicle screw 150, and FIG. 20 illustrates another kit 140 including an orthopedic pin 100 received within a channel of a surgical hammer 152. The use of the orthopedic pin with these and other medical devices benefits from the reduced-diameter portion as a feature of the orthopedic pin, which advantageously permits such devices to be slid over the proximal end of the orthopedic pin. This obviates the need to remove the orthopedic pin from a body into which it is inserted between different stages of a surgical procedure.

In summary, an orthopedic pin for optically analyzing a bone region has been described. The orthopedic pin includes an elongate shaft and at least one optical fiber. The elongate shaft has a circular outer cross section with a first diameter, a distal end for insertion into bone, a proximal end, and an optical connector portion disposed towards the proximal end. The at least one optical fiber extends within the elongate shaft between the optical connector portion, and the distal end for transmitting optical radiation between the optical connector portion and the bone region when the distal end is inserted into the bone region. The optical connector portion comprises a reduced-diameter portion. The reduced-diameter portion extends along at least a portion of the elongate shaft, and has an outer cross section comprising a width perpendicularly with respect to the elongate shaft. The width is less than the first diameter.

Various examples are provided above to show how the orthopedic pin interfaces with the optical adapter. If there is a single central optical fiber, this connection may be made with any relative angular orientation. The angular orientation may then be fixed or else the coupling between the orthopedic pin and the optical adapter may be free to rotate. If there are multiple optical fibers, the connection should be made between the orthopedic pin and the optical adapter with the correct relative angular orientation between the two components.

The optical adapter is shown as part of a handheld surgical tool. This gives a first possible configuration having a fiber-optic K-wire with the integrated optical fiber sensing, and a small detachable optical Spectroscopy Unit (OSU) in the form of a knob that is securely fixed such that it can rotate with the K-wire. Once the knob is detached, the fiber-optic K-wire can be inserted as a regular K-wire using regular placement tools. The knob can also operate as stand-alone OSU without fiber-optic connection with an external device.

An alternative configuration is the fiber-optic K-wire with the OSU integrated in a placement tool such as a drill. The fiber-optic K-wire is for example rigidly connected to the OSU, whereas the OSU allows rotation with respect to the placement tool. The coupling of the K-wire to this rotating OSU inside the placement tool may then use the reduced-diameter portion is as described above.

This allows placing of the K-wire using while performing spectral tissue sensing. If the fiber-optic K-wire is disconnected from the OSU (and therefore also from the placement tool), the fiber-optic K-wire can be used as regular K-wire in the sense that cannulated devices (e.g. pedicle screws) can be back-loaded from the proximal part. An advantage of this method is that the OSU and the placement tool are one device, thereby reducing the number of steps needed to use the fiber-optic K-wire.

Alternatively, the fiber-optic K-wire can be connected to and disconnected from the placement tool and the connection between the optical fibers of the K-wire and the placement tool may instead contain a rotating coupling (so the OSU is fixed relative to the placement tool). As mentioned above, the fiber-optic K-wire may contain one fiber on axis allowing a simple coupling since the fiber of the fiber-optic K-wire and the fiber to the OSU are both on axis and remain align also during rotation with respect to each other.

Alternatively, the fiber-optic K-wire may instead contain more than one fiber. In this case, fiber alignment needs to be ensured. This may involve use of a dual core fiber (in which case no special alignment is needed), or a central fiber and one or more concentric an off-axis fibers (e.g. a ring of annular fibers). A correct relative angular orientation is then needed to make the optical fiber coupling.

Various embodiments have been described in relation to an orthopedic pin, an optical adapter and a handheld surgical tool. For the sake of unnecessary duplication it is noted that the various features disclosed in relation to one embodiment may be combined with other embodiments in order to achieve the stated and further advantageous effects. Any reference signs in the claims should not be construed as limiting the scope of the invention.

The invention claimed is:

1. An orthopedic pin for optically analyzing a bone region, the orthopedic pin comprising:
    an elongate shaft having a circular outer cross section with a first diameter, a distal end for insertion into bone, a proximal end, and an optical connector portion disposed towards the proximal end; and
    at least one optical fiber extending within the elongate shaft between the optical connector portion and the distal end for transmitting optical radiation between the optical connector portion and the bone region when the distal end is inserted into the bone region; and
    wherein the optical connector portion comprises a reduced-diameter portion extending along a portion of the elongate shaft and having an outer cross section comprising a width perpendicular with respect to the elongate shaft, the width being less than the first diameter.

2. The orthopedic pin according to claim 1, wherein the reduced-diameter portion comprises a second circular outer cross section arranged coaxially with the circular outer cross section having the first diameter; and wherein the second circular outer cross section has a second diameter that is less than the first diameter.

3. The orthopedic pin according to claim 1, wherein the reduced-diameter portion comprises at least one a flat surface extending along the at least a portion of the elongate shaft.

4. The orthopedic pin according to claim 1, wherein the reduced-diameter portion comprises an outer cross section having only a single degree of rotational symmetry about a longitudinal axis of elongate shaft.

5. The orthopedic pin according to claim 1, wherein the reduced-diameter portion is separated from the proximal end of the elongate shaft by a proximal portion of the elongate shaft having an outer cross section comprising a minimum width perpendicular with respect to the elongate shaft and parallel to the width of the reduced-diameter portion that exceeds the width of the reduced-diameter portion and is less than or equal to the first diameter.

6. The orthopedic pin according to claim 1, further comprising:
    two or more optical fibers that each includes a proximal end disposed towards the distal end of the elongate shaft, wherein the proximal end of at least one of the two or more optical fibers is separated from the proximal end of at least another of the two or more optical fibers by a groove or a ridge or a step.

7. The orthopedic pin according to claim 1, further comprising:
    two or more optical fibers, wherein a distal end of at least one of the two or more optical fibers is configured to at least one of emit or receive optical radiation through an opening in the elongate shaft and in a radial direction with respect to the elongate shaft, and wherein a distal end of at least another of the two or more optical fibers is configured to at least one of emit or receive optical radiation through the distal end of the elongate shaft and in an axial direction with respect to the elongate shaft.

8. The orthopedic pin according to claim 1, further comprising:
    a first optical fiber and a second optical fiber, and
    wherein the elongate shaft further comprises a bore within which the first optical fiber and the second optical fiber extend, the bore including a central portion disposed between the optical connector portion of the elongate shaft and the distal end of the elongate shaft and within which central portion a longitudinal axis of the first optical fiber is maximally separated from a longitudinal axis of the second optical fiber by a first separation distance,
    wherein at least one of the optical connector portion of the elongate shaft or the distal end of the elongate shaft includes a transition region having a plug, the bore having a wider diameter in the transition region than in the central portion; and
    wherein the plug fits within the bore in the transition region and the plug is configured to separate the first optical fiber and the second optical fiber such that the longitudinal axis of the first optical fiber is separated from the longitudinal axis of the second optical fiber by a second separation distance, the second separation distance being greater than the first separation distance.

9. An optical adapter for releasably mating with the optical connector portion of the orthopedic pin according to claim 1, the optical adapter comprising:
    a port for receiving the proximal end of the elongate shaft including the reduced-diameter portion;

a gripping element; and at least one optical element for coupling optical radiation to the at least one optical fiber of the orthopedic pin; and wherein when the reduced-diameter portion of the elongate shaft is received within the port, the gripping element is configured to engage with the reduced-diameter portion of the elongate shaft such that the at least one optical element is aligned with the at least one optical fiber of the orthopedic pin for coupling optical radiation therebetween.

10. The optical adapter according to claim 9, wherein the gripping element comprises an engaging surface for engaging with the reduced diameter portion of the elongate shaft of the orthopedic pin; and wherein the gripping element is configured to move transversely with respect to a longitudinal axis of the elongate shaft of the orthopedic pin such that when the reduced-diameter portion of the elongate shaft is received within the port the engaging surface engages with the reduced-diameter portion of the elongate shaft.

11. The optical adapter according to claim 9, wherein the reduced-diameter portion of the elongate shaft of the orthopedic pin is separated from the proximal end of the elongate shaft by a proximal portion of the elongate shaft having an outer cross section comprising a minimum width perpendicularly with respect to the elongate shaft and parallel to the width of the reduced-diameter portion that exceeds the width of the reduced-diameter portion and is less than or equal to the first diameter; and wherein a transition between the reduced diameter portion and the proximal portion provides a step for retaining the orthopedic pin in the port; and wherein the gripping element includes a corresponding surface for engaging with the step when the reduced-diameter portion of the elongate shaft is received within the port such that the orthopedic pin is retained in the port.

12. A handheld surgical tool comprising:
the optical adapter according to claim 9;
a spectrometer comprising:
at least one optical source; and
at least one optical detector;
wherein the at least one optical source and the at least one optical detector are optically coupled to the at least one optical element and arranged such that when an orthopedic pin is received within the port of the optical adapter, and when the distal end of the elongate shaft of the orthopedic pin is inserted into the bone region, optical radiation generated by the at least one optical source irradiates the bone region via the at least one optical fiber, and optical radiation reflected or scattered by the bone region is optically coupled to the at least one optical detector via the at least one optical fiber; and a processor in communication with the spectrometer and is configured to:
cause the at least one optical source to generate the optical radiation for optically irradiating the bone region);
receive electrical signals generated by the at least one optical detector in response to optically irradiating the bone region;
process the received electrical signals with an algorithm configured to:
determine a first parameter indicative of a fat content or a water content in the bone region based on the received electrical signals; and
identify a type of the bone region based on the first parameter;
the type being at least one of cancellous bone and cortical bone.

13. The handheld surgical tool according to claim 12, wherein the algorithm is further configured to:
determine a second parameter indicative of at least one of a collagen content or optical scattering in the bone region; and
identify the type of the bone region based further on the second parameter.

14. The handheld surgical tool according to claim 12, wherein the algorithm is further configured to determine a blood content in the bone region, and further comprising an indicator; wherein the indicator is configured to generate:
a first output if the type of the bone region is cancellous bone;
a second output if the type of the bone region is cortical bone;
a third output indicative of a certainty of the identification of the type of the bone region, the third output being provided based on the determined blood content in the bone region.

15. A kit comprising
the orthopedic pin according to claim 1; and
at least one of:
a pedicle screw comprising a channel for receiving the elongate shaft of the orthopedic pin;
a hollow drill having a channel configured to receive the orthopedic pin;
a surgical screwdriver having a channel configured to receive the orthopedic pin;
a surgical hammer having a channel configured to receive the orthopedic pin.

* * * * *